US006213765B1

United States Patent
Standerwick et al.

(10) Patent No.: US 6,213,765 B1
(45) Date of Patent: Apr. 10, 2001

(54) ORTHODONTIC PROTRACTION APPLIANCE WITH HEAD-CHEST BRACING

(75) Inventors: R. William Standerwick, 6549 Fraser Street, Vancouver, British Columbia (CA), V5X 3T4; Eric B. Fetchko, Burnaby (CA)

(73) Assignee: R. William Standerwick (CA)

( * ) Notice: Subject to any disclaimer, the term of this patent is extended or adjusted under 35 U.S.C. 154(b) by 0 days.

(21) Appl. No.: 09/465,663

(22) Filed: Dec. 17, 1999

(51) Int. Cl.$^7$ ........................................................ A61C 3/00
(52) U.S. Cl. .................................................................. 433/5
(58) Field of Search ................................... 433/5; 602/17; 128/97.1, 857, 861

(56) References Cited

U.S. PATENT DOCUMENTS

| | | | |
|---|---|---|---|
| 862,881 | 8/1907 | Case | 433/5 |
| 2,151,458 | 3/1939 | Allen | 602/17 |
| 2,334,894 | 11/1943 | Atkinson | 433/5 |
| 2,735,424 | * 2/1956 | Benjamin | 602/17 |
| 3,391,693 | 7/1968 | Georgiade et al. | 602/17 |
| 4,951,655 | 8/1990 | MacMillan et al. | 128/76 R |
| 5,531,229 | 7/1996 | Dean et al. | 128/866 |
| 5,810,583 | * 9/1998 | Doyle | 433/5 |

* cited by examiner

Primary Examiner—John J. Wilson
Assistant Examiner—Melba Bumgarner
(74) Attorney, Agent, or Firm—Oyen, Wiggs, Green & Mutala

(57) ABSTRACT

An orthodontic protraction appliance in which an upper portion of a vertically extending rod is supported against a patient's forehead, with the lower portion of the rod being supported against the patient's chest. An elastic support is coupled to a central portion of the rod to anchor a plurality of elastic bands connected to braces attached to the patient's teeth. In one embodiment, the elastic support is slidably positionable along and releasably fastenable to the first rod. An upper portion of a second rod can be coupled to a head band encircling the patient's head, with a lower portion of the second rod being coupled to the elastic support, which is slidably positionable along and releasably fastenable to the second rod. In such case, the elastic support is coupled to the central portion of the first rod to permit unimpeded vertical movement of the first rod with respect to the elastic support. A lateral alignment mechanism can be coupled between the central portion of the first rod and the lower portion of the second rod, to maintain lateral alignment of the elastic support with respect to the first rod as the first rod moves vertically with respect to the elastic support. A lower end of the upper portion of the first rod can be pivotally connected to an upper end of the lower portion of the first rod to permit lateral movement of the upper and lower portions of the first rod with respect to the patient, while substantially preventing forward or rearward movement of the upper or lower portions of the first rod with respect to the patient.

38 Claims, 20 Drawing Sheets

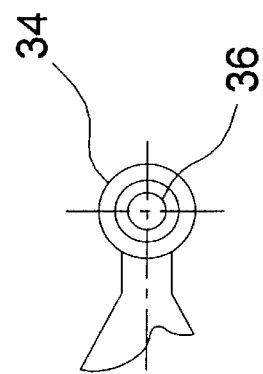
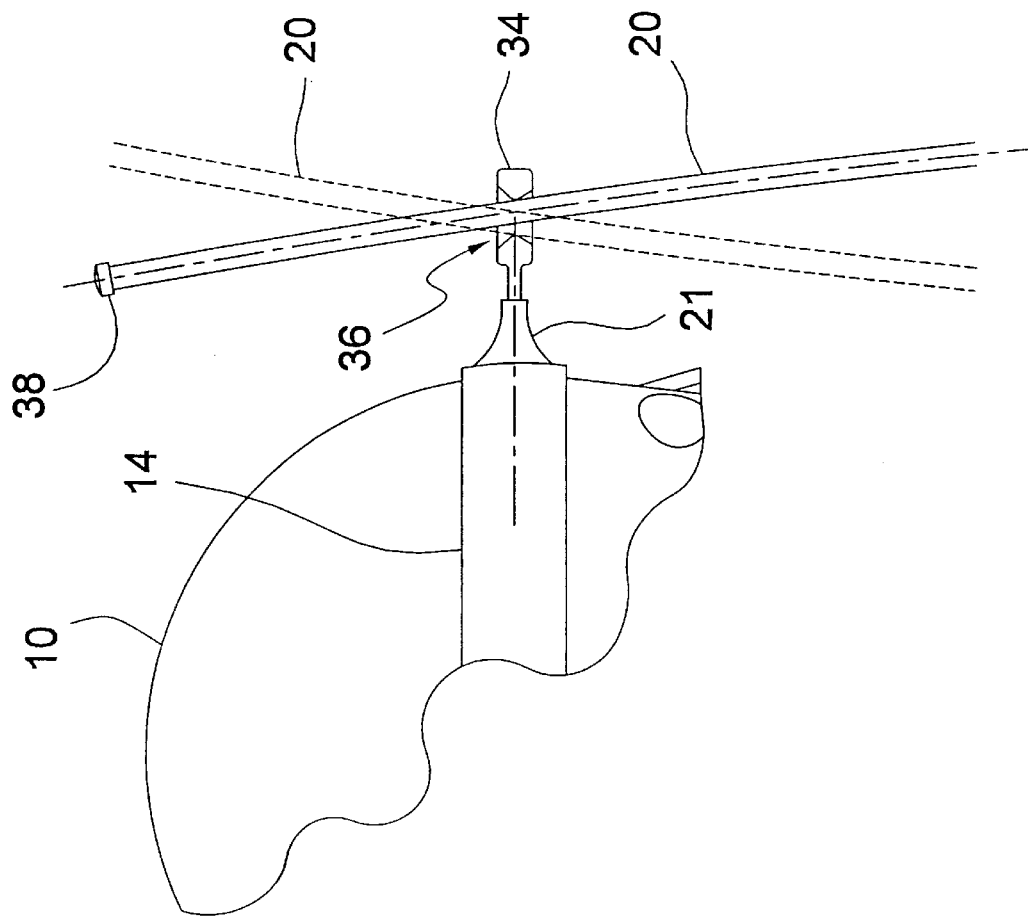
FIGURE 4
FIGURE 3

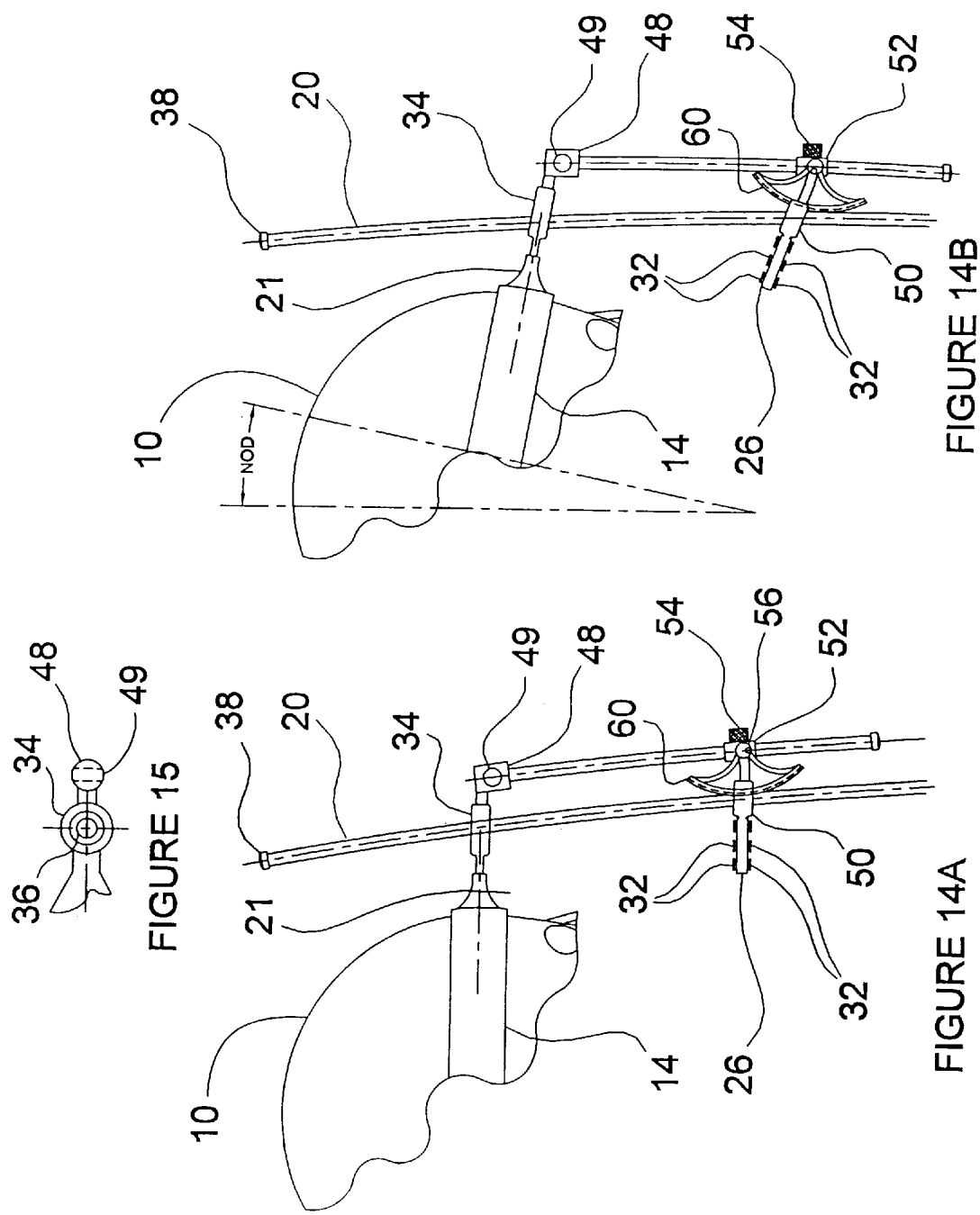

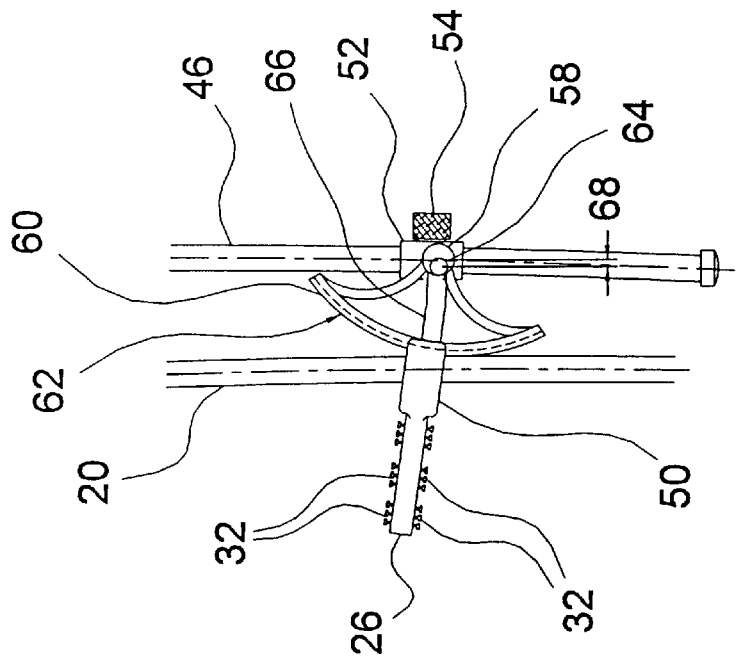
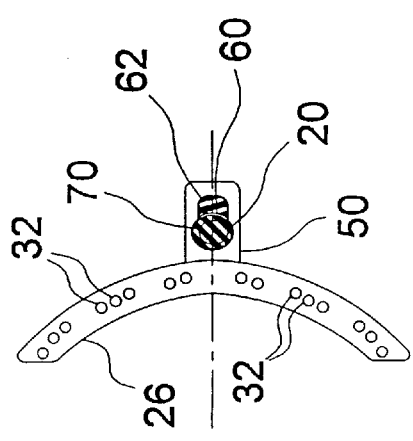
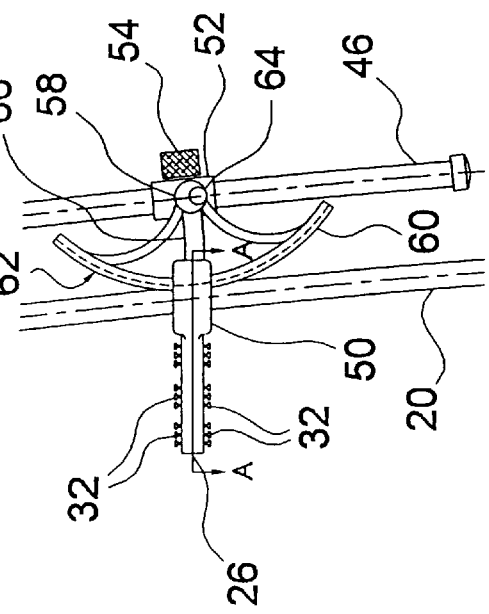

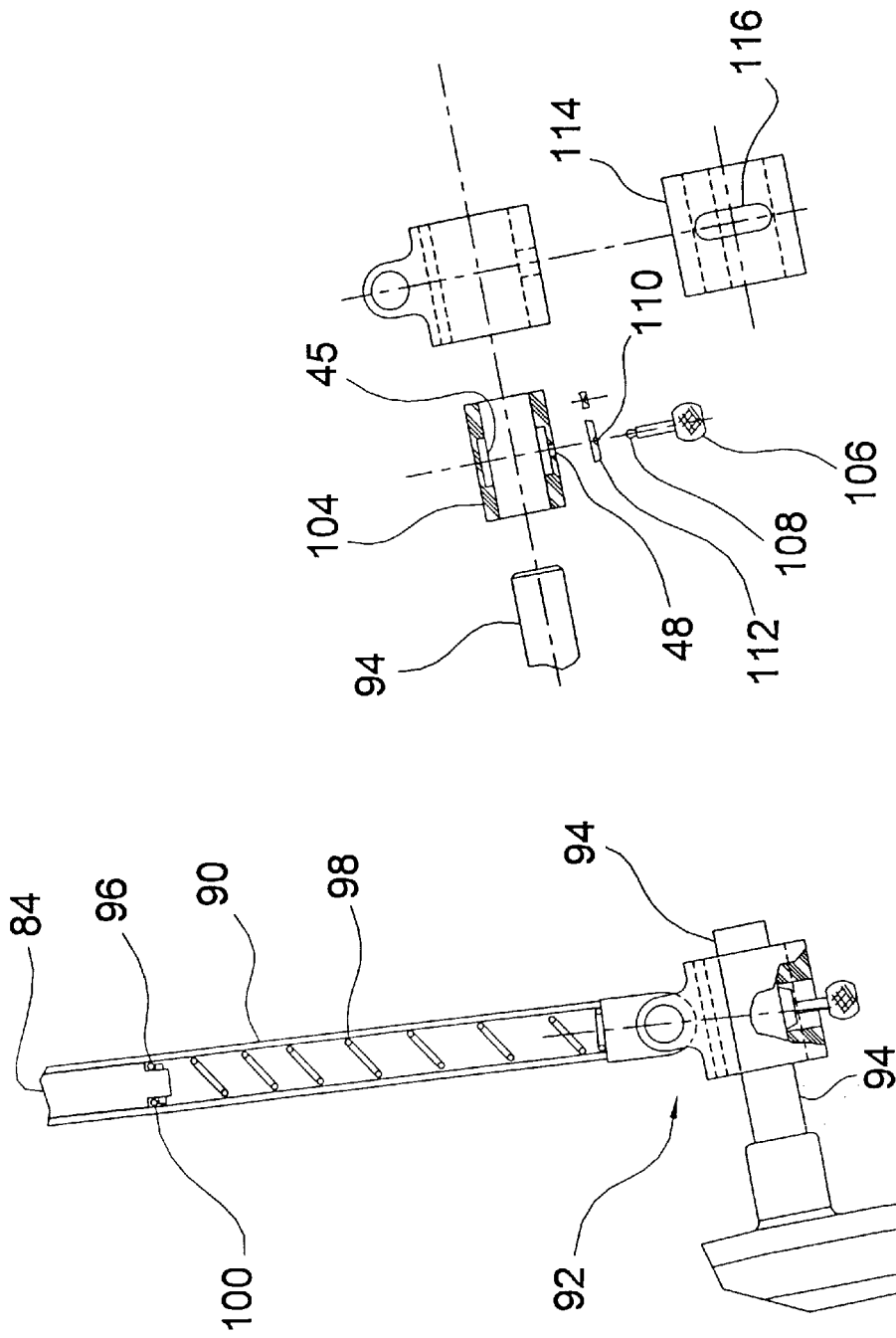

ORTHODONTIC PROTRACTION APPLIANCE WITH HEAD-CHEST BRACING

TECHNICAL FIELD

This application is directed to an orthodontic protraction appliance in which a rod is braced between a patient's forehead and chest (sternum). Elastics are mounted between the rod and orthodontic braces on the patient's teeth to apply the desired protracting force.

BACKGROUND

Orthodontists frequently find it necessary to apply protracting forces to a patient's teeth over prolonged periods of time. In some cases, the desired forces are preferably forwardly directed to urge the teeth outwardly away from the patient's mouth. The present invention provides a simple, stable device for applying such forces.

The prior art has evolved a variety of orthodontic protraction appliances. For example, U.S. Pat. No. 862,881 Case discloses a protraction appliance in the form of a headgear anchorage for applying corrective forces to the teeth. A retruding bow is held in front of the patient's mouth by elastic straps which form part of the headgear. The retruding bow can be connected to braces fixed to the patient's teeth to apply various forces to the teeth. Because the retruding bow is elastically supported at the back of the patient's head, Case's device is best suited to application of rearwardly directed forces and is generally incapable of applying significant forwardly directed forces in the manner of the present invention.

U.S. Pat. No. 2,334,894 Atkinson discloses an appliance having a frame which is strapped to a patient's head to position a spaced apart pair of parallel, vertical arms in front of the patient's face. A cross member extends horizontally between the arms. The ends of the cross member slidably engage the arms, allowing the cross member to be raised or lowered to position it at a desired level in front of the patient's mouth. Elastic bands, hooks, etc. can then be mounted between the cross member and braces applied to the patient's teeth, to apply the desired protracting force. Unlike the present invention, which provides secure bracing at the patient's forehead and sternum, Atkinson's device is braced between the patient's forehead and chin. Forehead-chin bracing is adequate to sustain application of corrective forces which are effective in some orthodontic correction procedures. However, forces imposed on the patient's lower jaw by an Atkinson type device can cause undesirable tempero mandibular joint displacement. This is preferably addressed by moving the maxillary posterior teeth forward, but such movement is not adequately achieved by the prior art.

SUMMARY OF INVENTION

The invention provides an orthodontic protraction appliance in which an upper portion of a vertically extending rod is supported against a patient's forehead, with the lower portion of the rod being supported against the patient's chest. An elastic support is coupled to a central portion of the rod to anchor a plurality of elastic bands connected to braces attached to the patient's teeth.

In a first embodiment, the elastic support is slidably positionable along and releasably fastenable to the first rod. The first support preferably includes a head band coupled to the upper portion of the rod. The head band encircles the patient's head to support the upper portion of the rod against the patient's head. The second support preferably includes a breast plate coupled to the lower portion of the rod. The breast plate supports the lower portion of the rod against the patient's chest. The opposed ends of a chest strap are coupled to the breast plate, and the chest strap is fastened to encircle the patient's chest and support the breast plate. A shoulder harness can be coupled between the breast plate and the chest strap, such that the shoulder harness extends over the patient's shoulders to further support the breast plate.

The first support further includes a first strut coupled between the upper portion of the rod and the head band. The second support further includes a second strut coupled between the lower portion of the rod and the breast plate. The first strut is coupled to the upper portion of the rod to permit unimpeded vertical movement of the rod with respect to the head band. This may be accomplished by fixing one end of the first strut to the head band and fixing an opposed end of the first strut to a first ring which encircles the upper portion of the first rod.

A second embodiment of the invention includes a second vertically extending rod. An upper portion of the second rod is coupled to the first support and a lower portion of the second rod is coupled to the elastic support. In the second embodiment: the elastic support is slidably positionable along and releasably fastenable to the second rod; and, head band additionally supports the upper portion of the second rod against the patient's head. The elastic support is coupled to the central portion of the first rod to permit unimpeded vertical movement of the first rod with respect to the elastic support. This may be accomplished by including in the elastic support further a second ring encircling the central portion of the first rod. Preferably, the upper portion of the second rod is pivotally coupled to the first support.

A third embodiment of the invention includes a lateral alignment mechanism coupled between the central portion of the first rod and the lower portion of the second rod to maintain lateral alignment of the elastic support with respect to the first rod as the first rod moves vertically with respect to the elastic support. The lateral alignment mechanism may be a sector with a vertical, concave groove in a rearward facing, convex arc portion of the sector. The groove is positioned against the central portion of the first rod to permit the sector to rotate along the groove with respect to the central portion of the first rod. A forward facing portion of the sector is pivotally coupled (preferably eccentrically) to the lower portion of the second rod. The elastic support and the sector's forward portion are slidably positionable along and releasably fastenable to the second rod. Advantageously, a second ring encircles the central portion of the first rod and further encircles the arc portion of the sector.

In a fourth embodiment of the invention, a lower end of the upper portion of the first rod is pivotally connected to an upper end of the lower portion of the first rod to permit lateral movement of the upper and lower portions of the first rod with respect to the patient, while substantially preventing forward or rearward movement of the upper or lower portions of the first rod with respect to the patient. Advantageously, the upper portion of the first rod is shaped to conform generally to a central vertical side profile of a human face, enabling the upper portion to be positioned closely to the face and thus reduce obstruction of the patient's vision. A universal joint pivotally couples the lower end of the lower portion of the first rod to the breast plate. The universal joint permits lateral movement of the lower portion of the first rod with respect to the patient, while substantially preventing forward or rearward movement of the lower portion of the first rod with respect to the patient. A spring coupled between the universal joint and the lower end of the lower portion of the first rod, biases the lower portion of the first rod away from the universal joint as the lateral movement increases, and assists in retracting the lower portion of the first rod toward the universal joint as the lateral movement decreases.

BRIEF DESCRIPTION OF DRAWINGS

FIG. 3 is an enlarged, partially fragmented side elevation view of the upper portion of the apparatus and patient depicted in FIG. 1.

FIG. 4 is a top plan view of the rod ring support depicted in FIGS. 1 and 3.

FIG. 6B additionally showing a head band snap connector in the opened position.

FIGS. 14A and 14B are partially fragmented, enlarged side elevation views of the upper portion of the patient and apparatus of FIGS. 12 and 13, depicting movement of the apparatus to accommodate movement of the patient's head.

FIG. 15 is a top plan view of the rod ring support and secondary guide rod support portions of the apparatus shown in FIGS. 12 and 13.

FIGS. 16A and 16B are respectively enlarged side elevation views of the central portions of the rod and secondary rod components of the apparatus of FIGS. 12 and 13, showing articulation of the sector to accommodate movement of the patient's head.

FIG. 17 is a cross-sectional view taken with respect to line A—A of FIG. 16A.

FIG. 23 is an enlarged, partially sectioned, side elevation view of the chest bracing and lower rod portion of the apparatus depicted in FIG. 18.

FIG. 24 is an exploded side elevation view of the universal joint components depicted in FIG. 23.

DESCRIPTION

Figure 1:
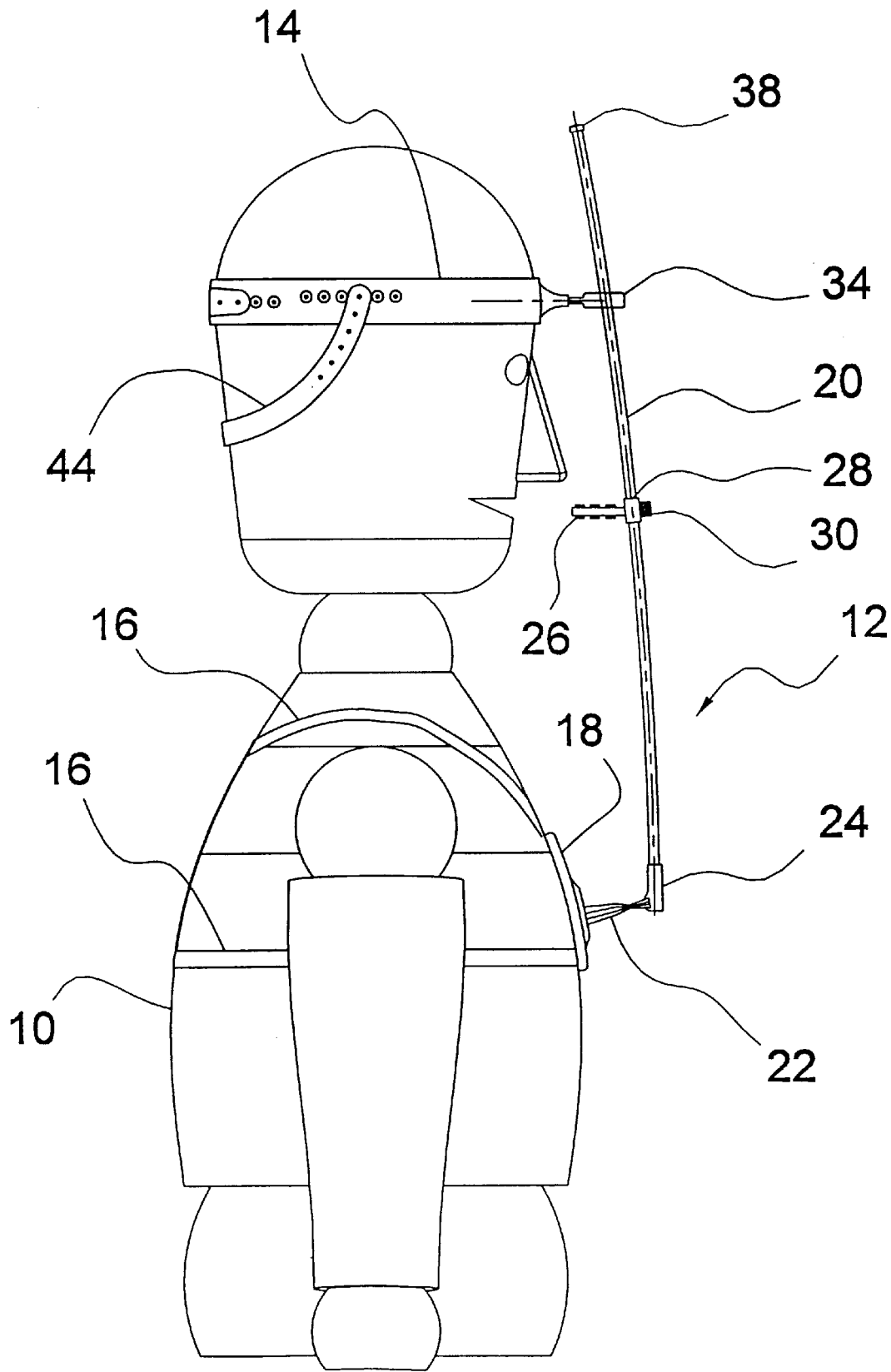
FIG. 1 is a side elevation view which schematically depicts a patient wearing an orthodontic protraction appliance constructed in accordance with a first embodiment of the invention.
Figure 2:
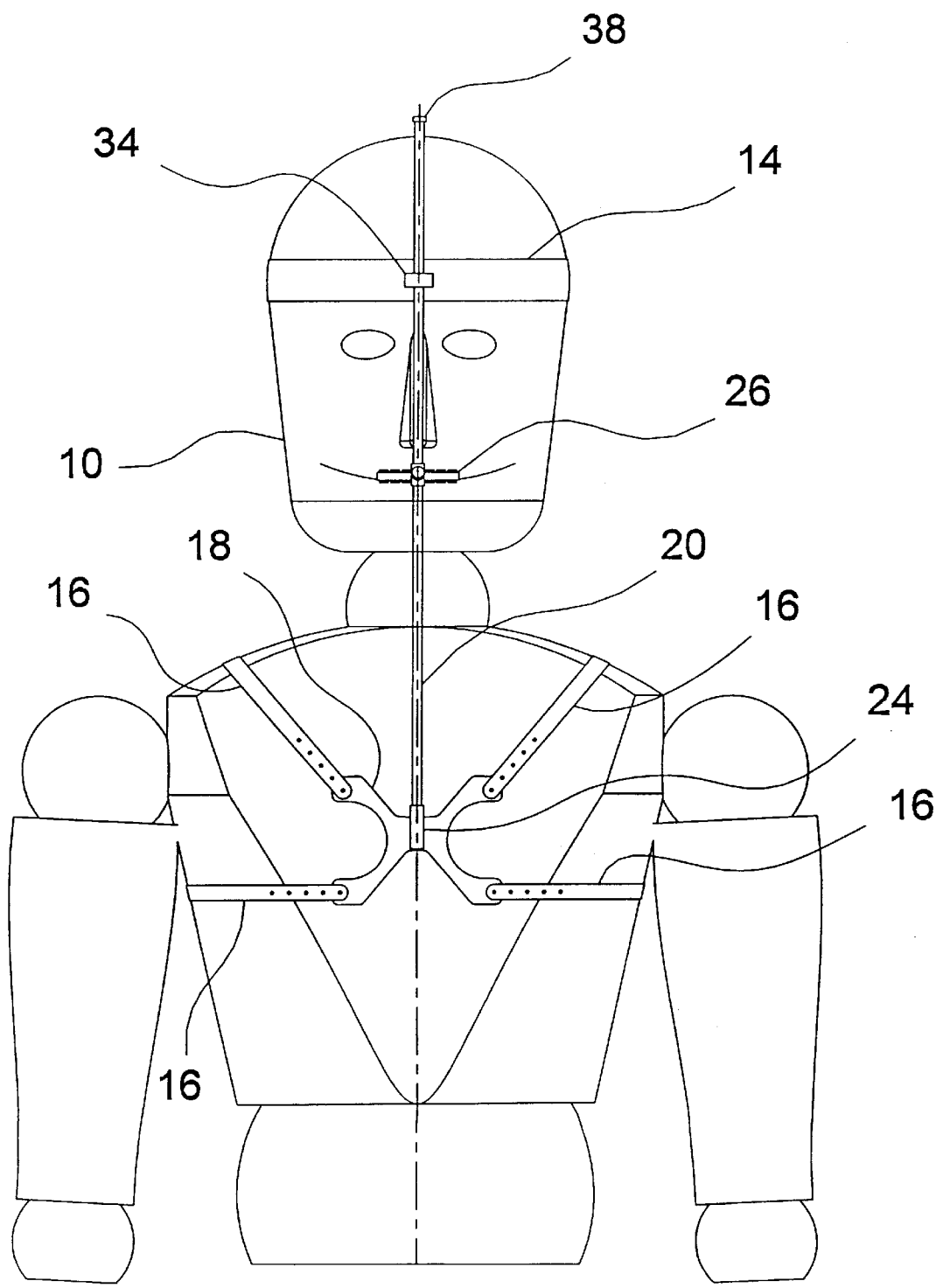
FIG. 2 is a front elevation view of the patient and apparatus of FIG. 1.
Figure 5B:
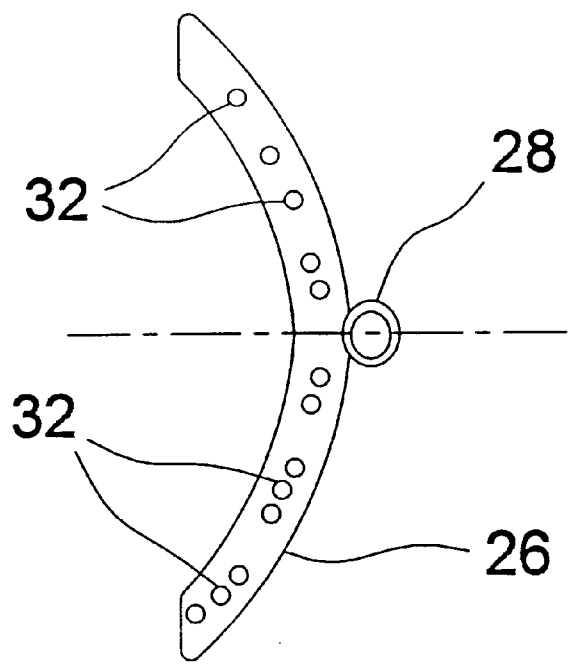
FIGS. 5A and 5B are respectively enlarged side elevation and top plan views of the elastic support plate depicted in FIGS. 1 and 2.
Figure 5A:
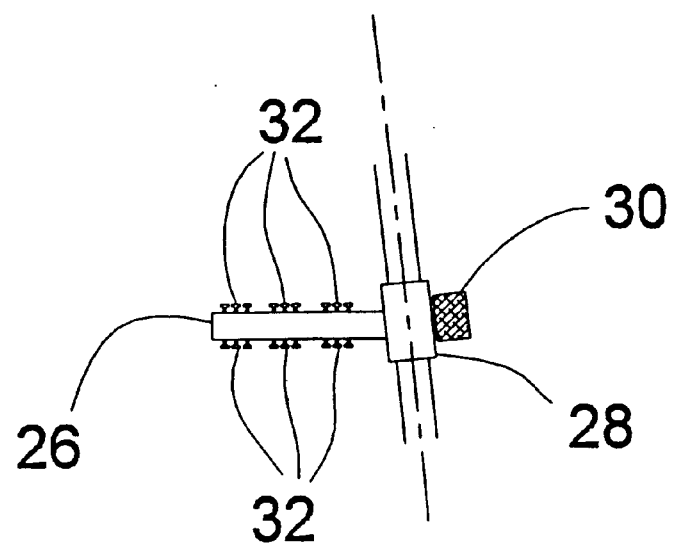
Figure 7A:
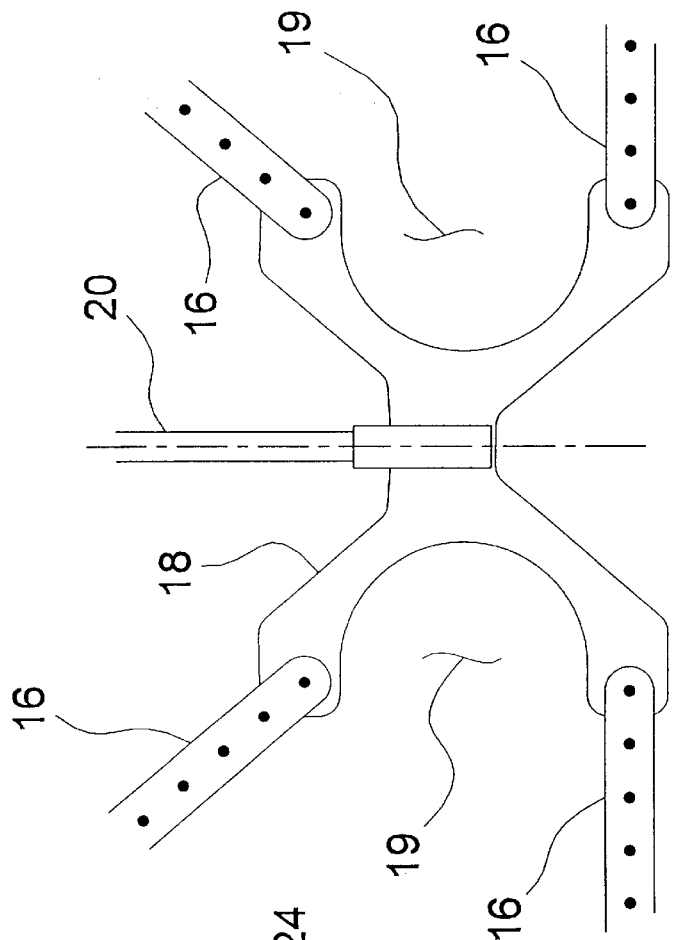
FIGS. 7A and 7B are respectively front plan and side elevation views of the breast plate portion of the apparatus depicted in FIGS. 1 and 2.
Figure 7B:
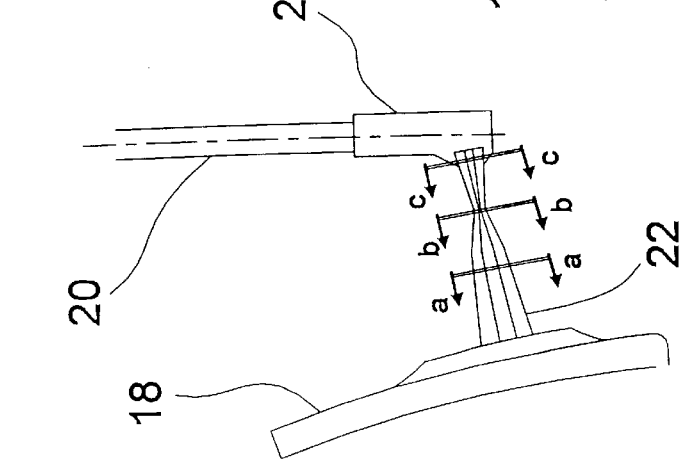
Figure 7C:
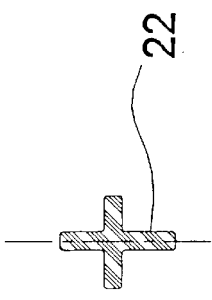
FIG. 7C is a cross-sectional view taken with respect to line A—A of FIG. 7B.
Figure 7D:
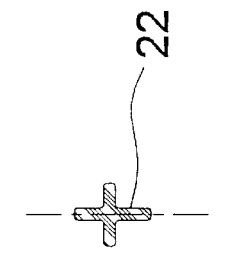
FIG. 7D is a cross-sectional view taken with respect to line B—B of FIG. 7B.

FIGS. 1 and 2 schematically depict a patient 10 wearing an orthodontic protraction appliance 12 constructed in accordance with a first embodiment of the invention. Apparatus 12 incorporates a head band 14 which is releasably adjusted to fit the patient's head in a comfortable position. Apparatus 12 also incorporates a harness 16 comprising a pair of shoulder straps and a chest-encircling strap, as illustrated. The frontal ends of the shoulder straps and the opposed ends of the chest-encircling strap are connected to the four opposed corners of breast plate 18, as best seen in FIGS. 2 and 7A. The rearward ends (not shown) of the shoulder straps are connected to the chest-encircling strap adjacent the patient's back. Breast plate 18 is formed so that it may be comfortably worn by male or female patients. In particular, breast plate 18 is provided with semi-circular cutouts 19 so that it may be worn in bra-type fashion by female patients.

Figure 7E:
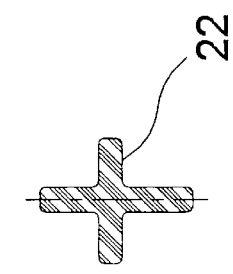
FIG. 7E is a cross-sectional view taken with respect to lines C—C of FIG. 7B.
Figure 8:
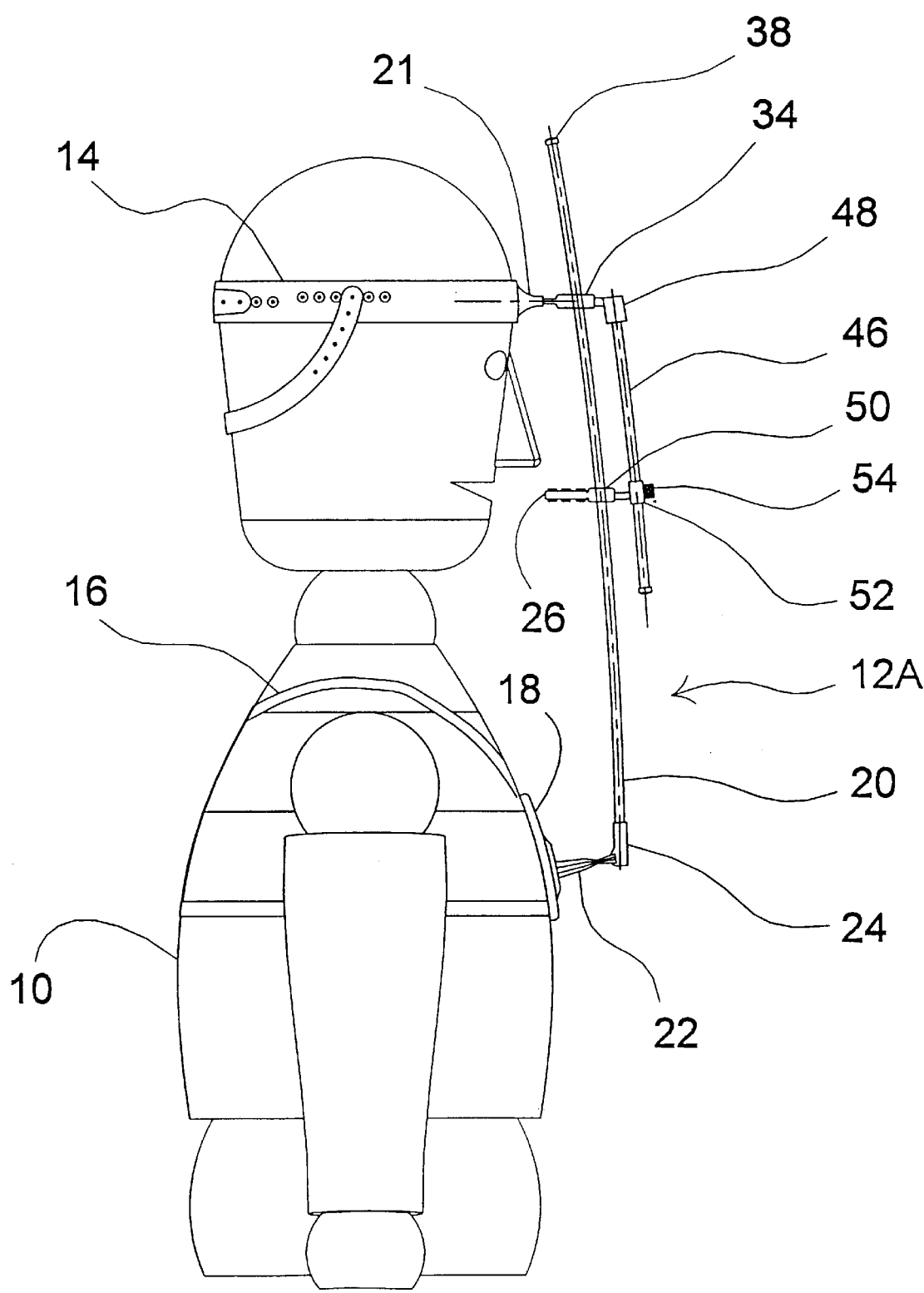
FIG. 8 is a side elevation view of a schematically illustrated patient wearing an orthodontic protraction appliance constructed in accordance with a second embodiment of the invention.
Figure 9:
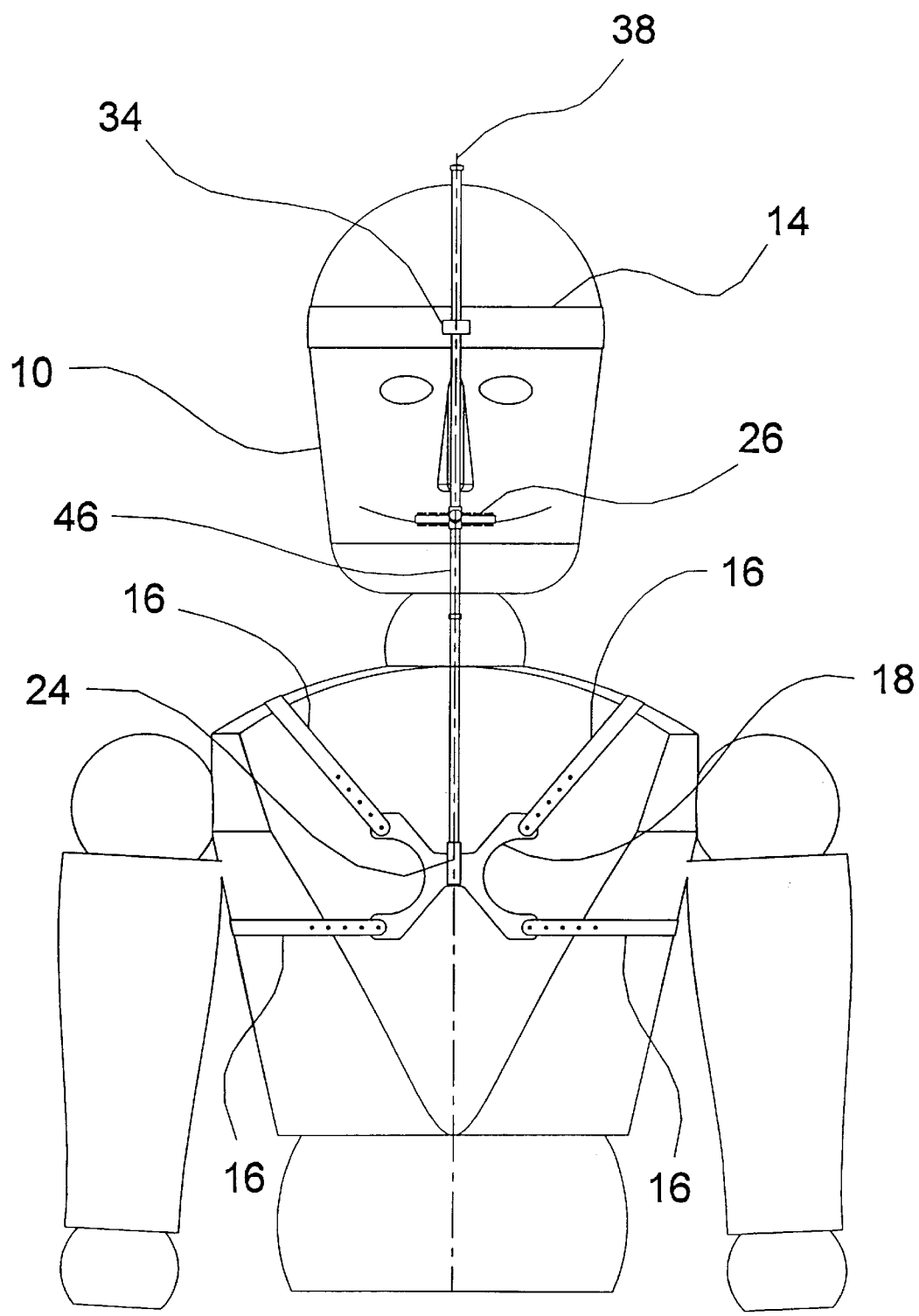
FIG. 9 is a front plan view of the patient and apparatus of FIG. 8.
Figure 11:
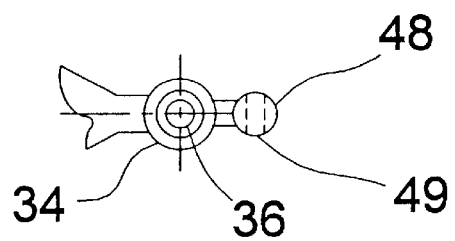
FIG. 11 is a top plan view of the rod ring support and secondary guide rod of the apparatus depicted in FIGS. 8 and 9.

A rigid "first" rod 20 formed of a material such as graphite fibre, fibreglass or stainless steel is semi-rigidly fixed to extend between first strut 21 on head band 14 and second strut 22 on breast plate 18. More particularly, the lower end of rod 20 is coupled to the central portion of breast plate 18 by second strut 22 which acts as a flexible, cantilevered beam and may be formed of a plastic or composite material having an inward end fixed to breast plate 18 and an outward end fixed to socket 24 within which the lower end of rod 20 is firmly retained. As best seen in FIGS. 7B through 7E, the cross-sectional area of second strut 22 is relatively large at the beam's point of affixation to breast plate 18 to provide rigid support and assist in distributing the load supported by second strut 22 over breast plate 18. The opposed outward end of second strut 22 fixed to socket 24 may have a somewhat smaller cross-sectional area, as seen in FIG. 7E. The central portion of second strut 22 preferably has a cross-sectional area (FIG. 7D) considerably smaller than the cross-sectional area at either of the beam's opposed ends. This enables second strut 22 to act as a "live hinge" providing slightly fettered movement in all directions. The reduced cross-sectional area in the central region of beam 22 reduces the beam's polar moment of inertia in such region and hence improves the beam's ability to flex and/or slightly rotate in such region, thus accommodating nodding and/or side-to-side movements of the patient's head.

An elastic support plate 26 is coupled to rod 20 by sliding rod 20 through apertured collar 28 fixed on the central outward facing portion of elastic support plate 26. Knurled adjustment screw 30 is tightened to releasably clamp elastic support plate 26 in a selected height position on rod 20 adjacent the patient's mouth. Elastic bands (not shown) are coupled by the orthodontist between selected points on braces (not shown) fixed to the patient's teeth and selected ones of protrusions 32 provided on the upper and lower surfaces of elastic support plate 26.

A "first" rod support ring 34 is fixed to and protrudes forwardly from the central forward portion of head band 14, as best seen in FIGS. 3 and 4. Rod 20 passes freely through aperture 36 in ring 34. Aperture 36 is radiused, and ring 34 is made of a suitable hard material to prevent stiction between rod 20 and ring 34 as rod 20 moves relative to ring 34 thus permitting unimpeded vertical (as viewed in FIG. 2) movement of rod 20 with respect to head band 14. These features assist in accommodating unfettered movement of the patient's head as illustrated by the solid and dashed line representations of rod 20 in FIG. 3. A rubber cap 38 may be provided atop rod 20 to protect objects which the top portion of rod 20 may inadvertently momentarily contact. The diameter of cap 38 preferably exceeds the diameter of aperture 36 to prevent inadvertent dislodgement of rod 20 from within ring 34 due to unexpected extreme backward movement of the patient's head.

Figure 6B:
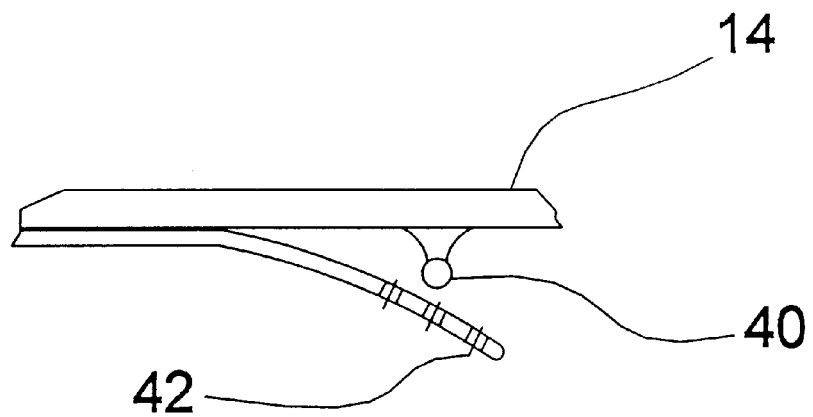
FIGS. 6A and 6B are respectively enlarged side elevation and top plan views of the adjustable head band portion of the apparatus depicted in FIGS. 1 and 2.
Figure 6A:
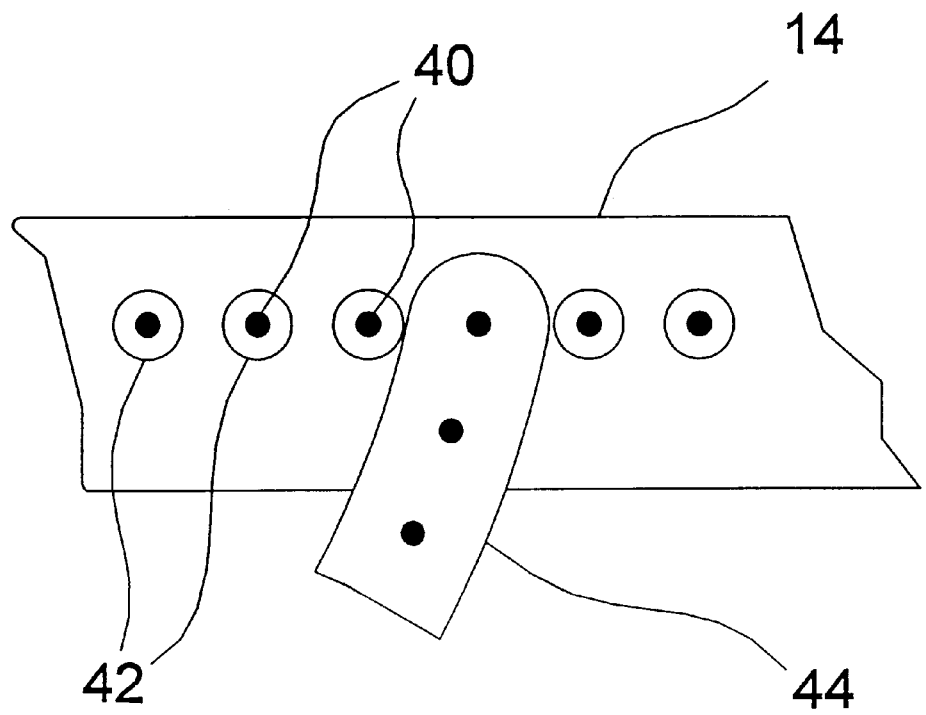

As seen in FIGS. 6A and 6B, head band 14 may be formed of plastic with a plurality of integral plastic knobs 40, each of which can be releasably snap-fitted into a selected one of a plurality of mating apertures 42 provided in head band 14. A secondary strap 44 may be similarly snap-fitted to head band 14 and extended behind the lower portion of the patient's head to provide additional support. As an alternative to knobs and apertures 40, 42 one may use VELCRO™ hook and loop type fastener to removably attach head band 14 around the patient's head.

FIGS. 8–11 depict a second embodiment of the invention, namely orthodontic protraction appliance 12A. Components of apparatus 12A which are identical to corresponding components of apparatus 12 depicted in FIGS. 1–7E have been given identical reference numerals in FIGS. 8–11 and will not be described further.

Apparatus 12A incorporates a "second" rod 46 which is mounted in front of rod 20 by fixing the upper end of rod 46 in socket 48, which is in turn fixed to and protrudes forwardly from the central forward portion of support ring 34. The upper end of secondary rod 46 is held within socket 48 by pivot pin 49 to permit forward and rearward pivotal movement of rod 46 with respect to ring 34, while preventing lateral movement of rod 46 with respect to ring 34.

Instead of releasably attaching elastic support plate 26 to rod 20 via adjustment screw 30 as in the case of apparatus 12, elastic support plate 26 in apparatus 12A is slidably positionable along and releasably fastenable to second rod 46. Specifically, a second ring 50 is fixed to the central forward portion of elastic support plate 26. Rod 20 passes freely through the aperture in ring 50 for stiction-free movement of the central portion of rod 20 relative to ring 50. Apertured collar 52 is fixed to and protrudes forwardly from the central forward portion of ring 50. Secondary rod 46 slides through collar 52 and is releasably fastened with respect to collar 52 by tightening knurled adjustment screw 54.

Figure 10:
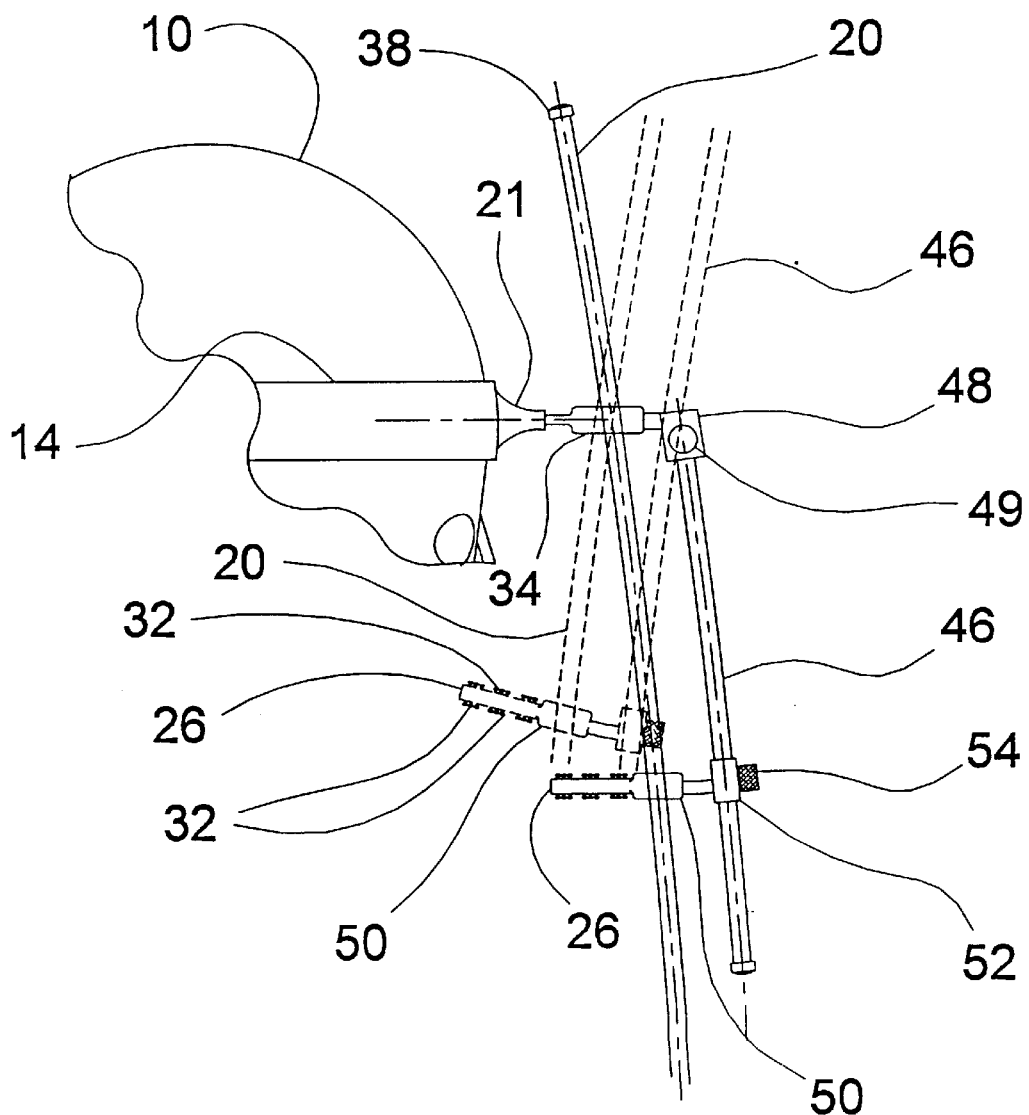
FIG. 10 is a partially fragmented, enlarged side elevation view of the upper portion of the apparatus and patient depicted in FIGS. 8 and 9.
Figure 12:
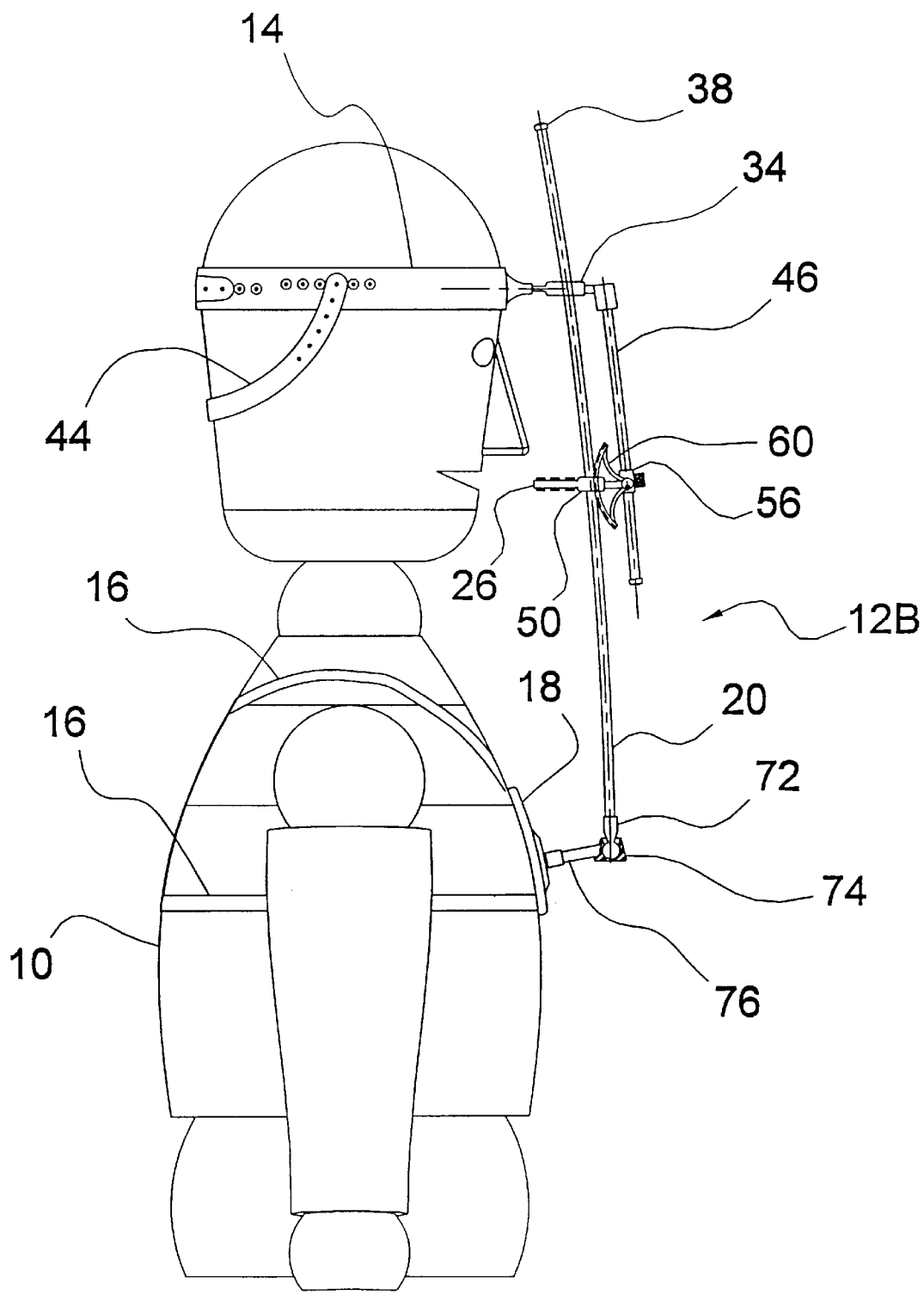
FIG. 12 is a side elevation view of a schematically illustrated patient wearing an orthodontic protraction appliance constructed in accordance with a third embodiment of the invention.
Figure 13:
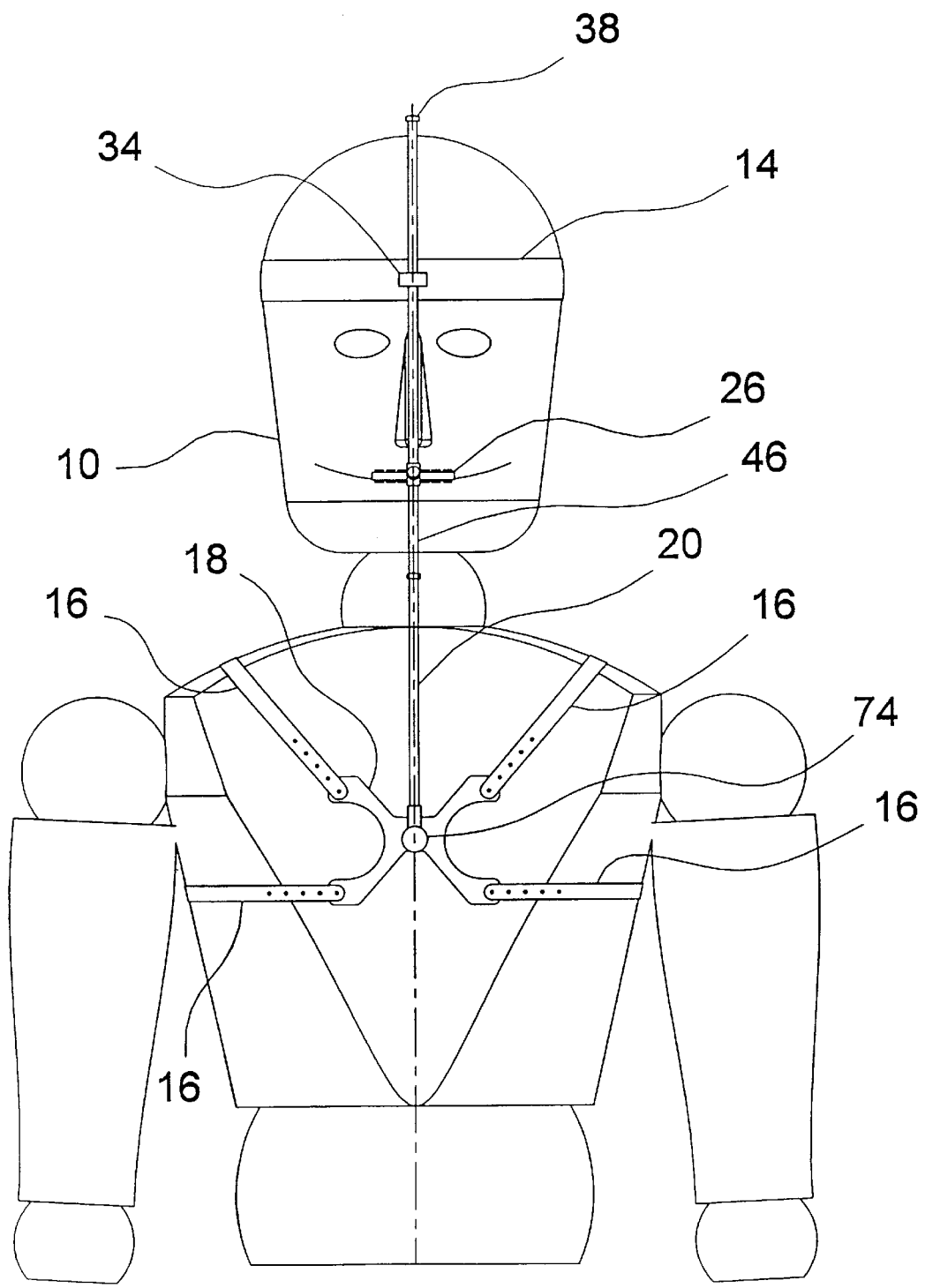
FIG. 13 is a front plan view of the patient and apparatus of FIG. 12.

The second embodiment of FIGS. 8–11 enables elastic support plate 26 to flex rearwardly with the patient's mouth as the patient's forehead nods forwardly, as indicated by the dashed and solid line positions of rods 20, 46 in FIG. 10.

FIGS. 12–17 depict a third embodiment of the invention, namely orthodontic protraction appliance 12B. Components of apparatus 12B which are identical to corresponding components of apparatus 12 depicted in FIGS. 1–7E and/or identical to corresponding components of apparatus 12A depicted in FIGS. 8–11 have been given identical reference numerals in FIGS. 12–17 and will not be described further.

Apparatus 12B includes a "lateral alignment means" which is coupled between the central portion of first rod 20 and the lower portion of second rod 46 to maintain lateral alignment of elastic support plate 26 with respect to rod 20 as rod 20 moves vertically (due to movement of the patient's head) with respect to elastic support plate 26. Specifically, a clevis arrangement 56 is pivotally coupled to collar 52 by pin 58. The rearward convex arc portion of sector 60 passes through the aperture in ring 50, such that the rearward convex arc portion of sector 60 bears against the frontal portion of rod 20 within ring 50. A longitudinally extending concave groove 62 is provided in the rearward convex arc portion of sector 60, such that rod 20 remains laterally aligned within groove 62 as sector 60 rotates with respect to rod 20.

More particularly, as the patient's head nods forwardly from the position shown in FIG. 14A to that shown in FIG. 14B, elastic support plate 26 moves upwardly through an arc, thereby causing relative rearward arcuate movement of rods 20, 46. Such relative movement rotates sector 60 about pivot pin 58 relative to collar 52. As pin 58 rotates it moves pin 64 which is eccentrically mounted on pin 58 as seen in FIGS. 16A and 16B. Eccentric pin 64 is fixed to the frontal forward portion of ring 50 by strut 66. Accordingly, eccentric motion of pin 64 with respect to pin 58 moves strut 66 and thus elastic support plate 26 forwardly or rearwardly with respect to the patient's teeth as sector 60 rotates about its above-described eccentric mounting on rod 46. By varying the displacement between the centres of pins 58, 64 one may adjust the eccentric travel displacement (indicated at 68) as the patient's head nods back and forth, thus accommodating varying head and facial sizes and relative motions of different patients and thereby maintaining generally consistent tension in the elastic bands (not shown) coupled by the orthodontist between selected points on braces (not shown) fixed to the patient's teeth and selected ones of protrusions 32 provided on the upper and lower surfaces of elastic support plate 26.

As seen in FIG. 17, the aperture in ring 50 has a key slot shape to accommodate rod 20 and sector 60 in a manner which prevents binding between these parts when the patient's head nods or is turned from side-to-side.

A ball 72 (FIG. 12) is rigidly fixed to the lower end of rod 20. Ball 72 is rotatably supported within socket 74 which is in turn fixed to the central frontal forward portion of breast plate 18 by strut 76. This ball and socket joint permits reasonably unfettered motion of the lower end of rod 20 in all directions. In contrast to the "live hinge" described above with reference to apparatus 12 of FIGS. 1–7E, the ball and socket joint provided in the FIG. 12B apparatus is less resistive to motion of the lower end of rod 20, thus precluding possible unintended flexing of rod 20 and consequential undesirable changes in the tension imparted to the elastics (not shown) fixed between support plate 26 and the patient's teeth.

FIGS. 18–24 depict a fourth embodiment of the invention, namely orthodontic protraction appliance 12C. Components of apparatus 12C which are identical to corresponding components of apparatus 12 depicted in FIGS. 1–7E and/or identical to corresponding components of apparatus 12A depicted in FIGS. 8–11 and/or identical to corresponding components of apparatus 12B depicted in FIGS. 12–17 have been given identical reference numerals in FIGS. 18–24 and will not be described further.

An upper rigid rod 78 which may for example be formed of stainless steel is fixed at its upper end to the central frontal forward portion of head band 14. This is accomplished by fitting the upper end of rod 78 within socket 80 fixed on head band 14. Ribs 82 are formed on head band 14 and extend laterally to either side of socket 80 to assist in stabilizing the upper end of rod 78.

Figure 21:
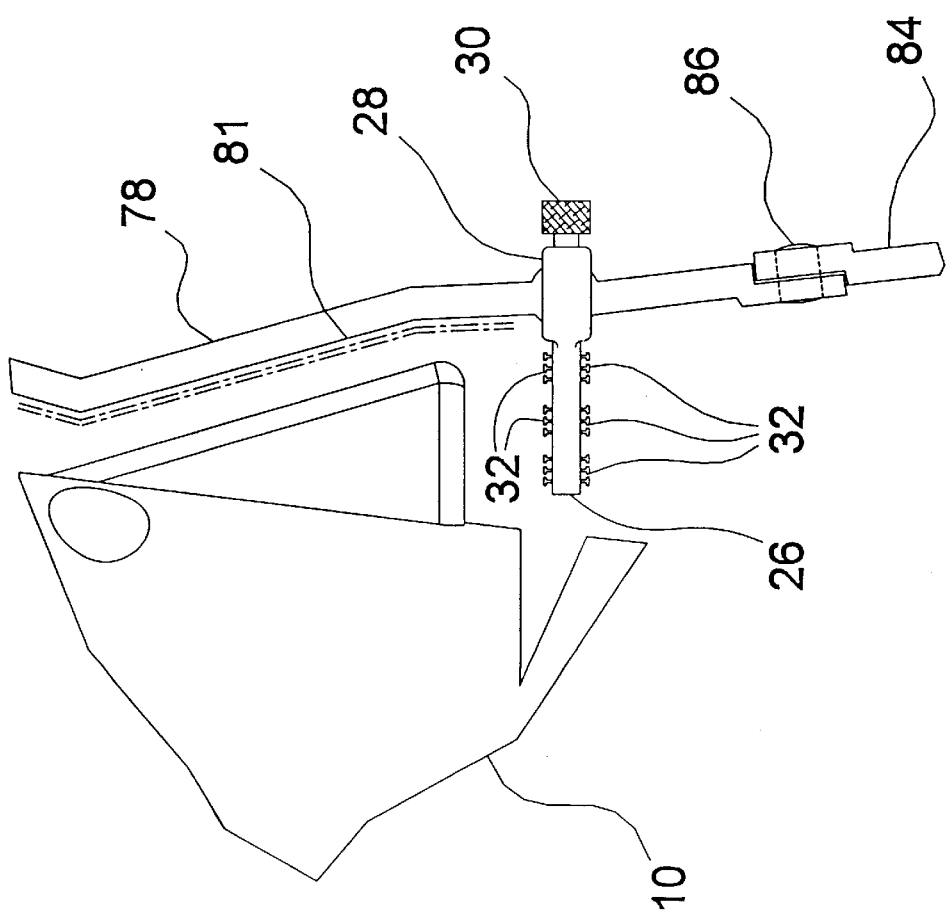
FIG. 21 is an enlarged side elevation view of the facial portion of the patient and adjacent apparatus of FIG. 18.

As shown in FIG. 21, upper rod 78 is formed in a shape which generally conforms to the central vertical side portion of the typical human facial profile, as indicated by profile line 81. This enables rod 78 to be located more closely to and centered with respect to the patient's face, thus assisting in maintaining rod 78 inside the focal point of the patient's eyes, minimizing possible obstruction of the patient's vision. Moreover, location of rod 78 more closely to the patient's head reduces the mechanical advantage to which head band 14 is subjected by forces imparted to rod 78.

The upper end of lower rod 84 is coupled to the lower end of upper rod 78, as best seen in FIG. 21. More particularly, the lower end of rod 78 and the upper end of rod 84 each have a flat profile. The flattened rod ends are pivotally connected to one another by pin 86. This allows the rods' ends to pivot laterally in the direction of double-headed arrow 88 (FIG. 22) and in a plane generally parallel to the patient's chest, while substantially preventing forward or rearward movement of the rods' ends. Thus, motion like that made if the patient's head is shaken from side to side (i.e. to indicate "no") is accommodated.

The lower end of rod 84 is slidably disposed within the upper end of tubular rod 90. The lower end of rod 90 is coupled to universal joint 92 (FIG. 23) which is in turn coupled to the outward end of strut 94. The opposed, inward end of strut 94 is fixed to the central frontal portion of breast plate 18.

Figure 18:
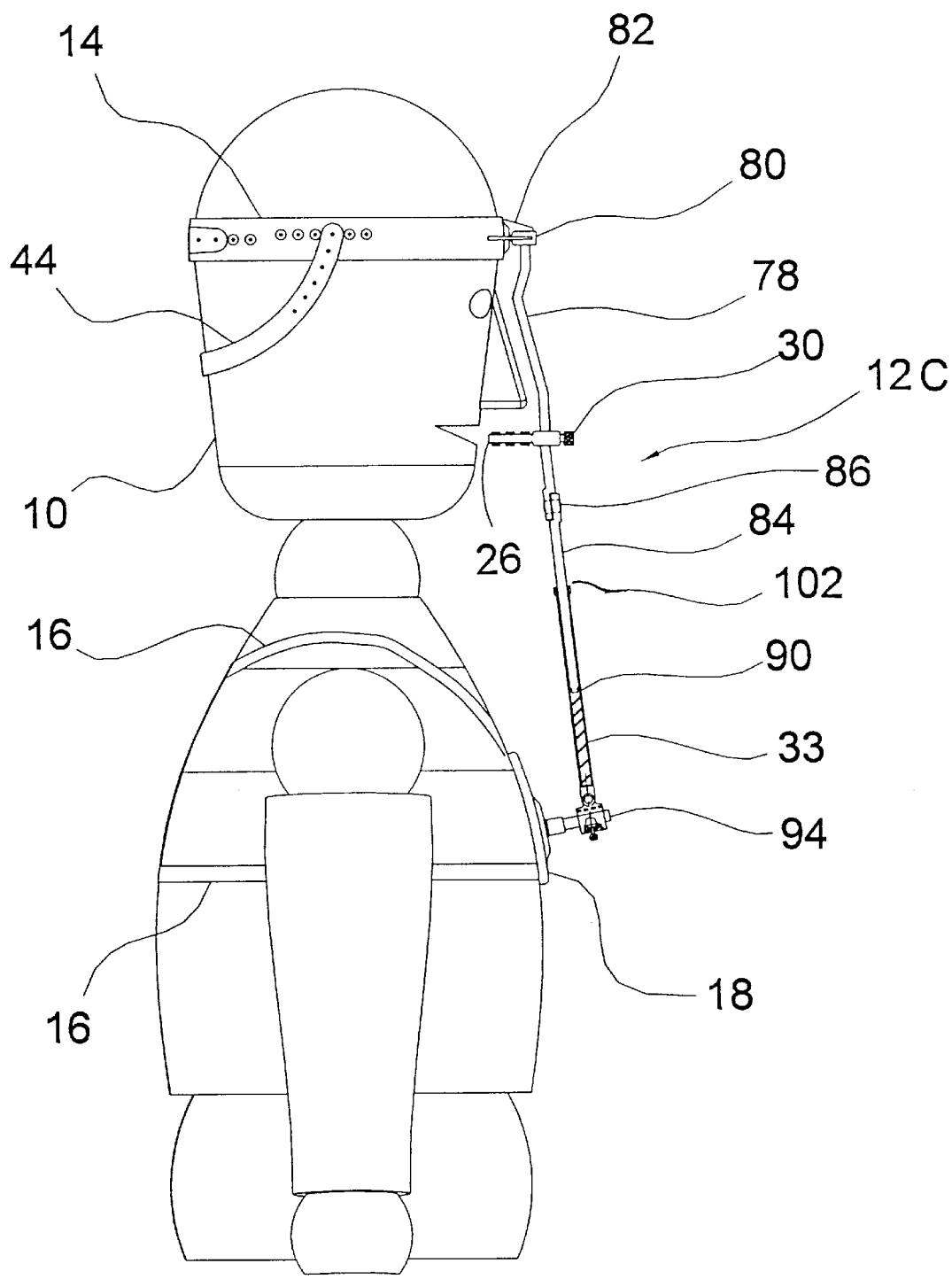
FIG. 18 is a side elevation view of a schematically illustrated patient wearing an orthodontic protraction appliance constructed in accordance with a fourth embodiment of the invention.
Figure 20:
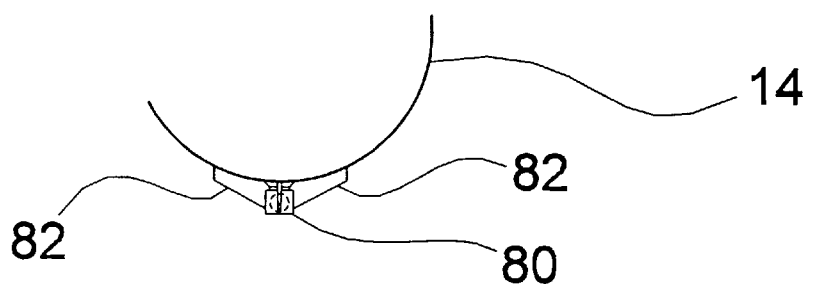
FIG. 20 is a top plan view of a frontal segment of the head band portion of the apparatus depicted in FIG. 19.
Figure 19:
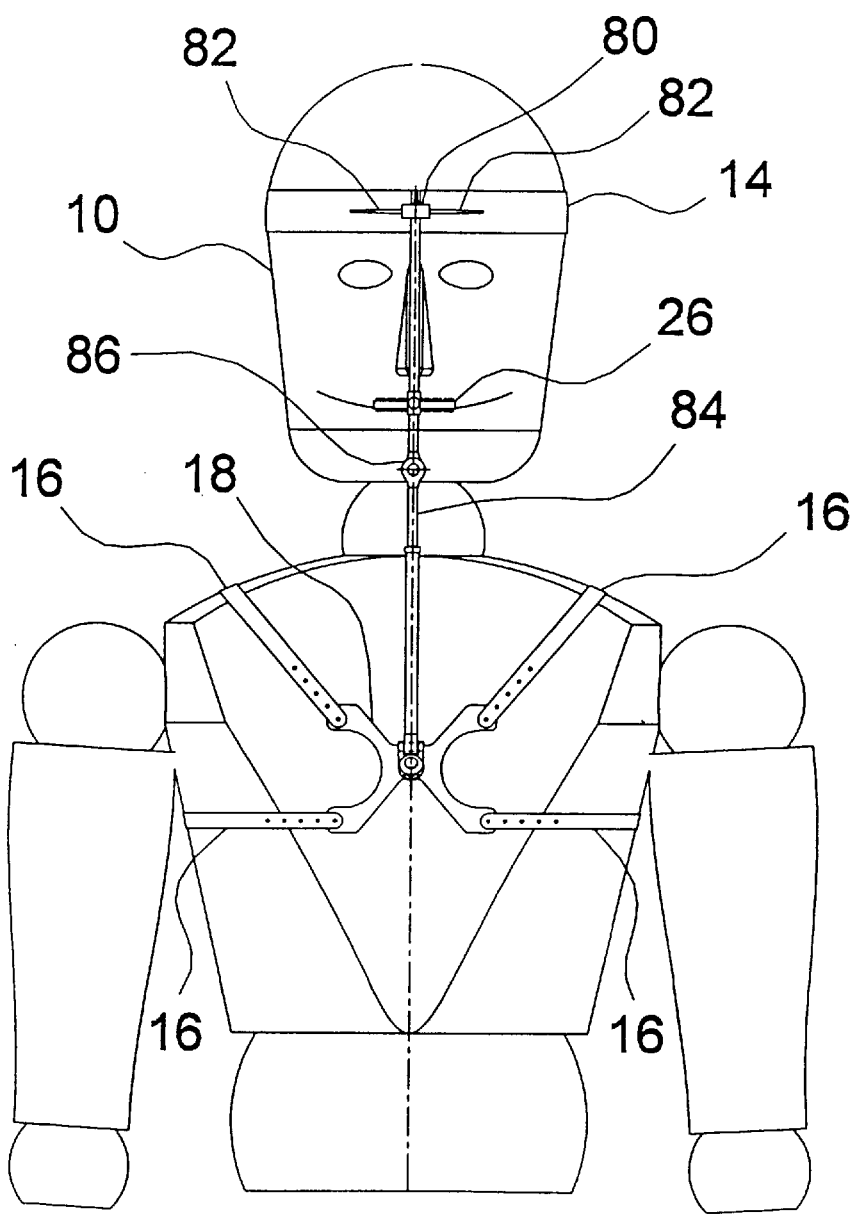
FIG. 19 is a front plan view of the patient and apparatus of FIG. 19.
Figure 22:
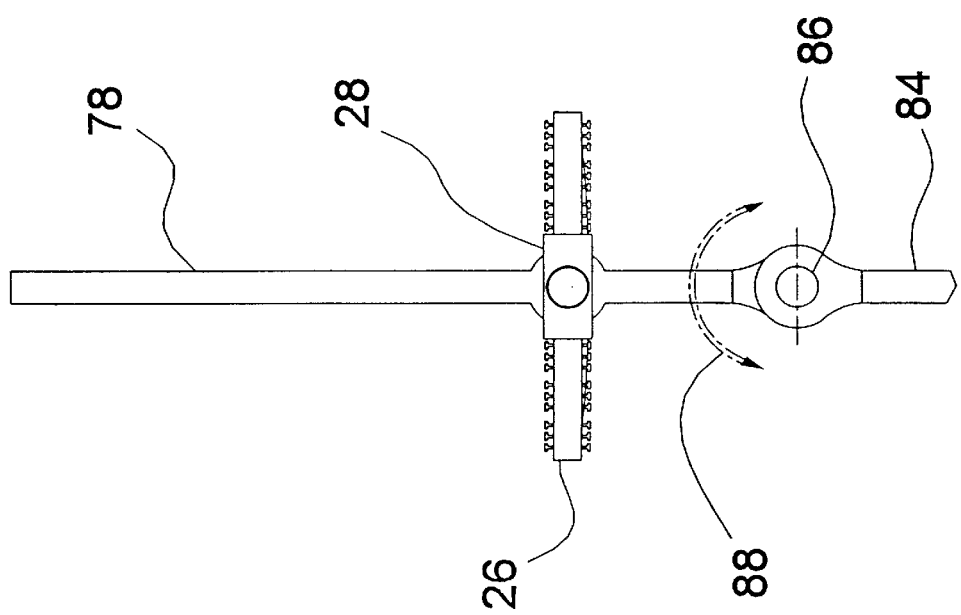
FIG. 22 is a front plan view of the portion of the apparatus depicted in FIG. 21.
Figure 25:
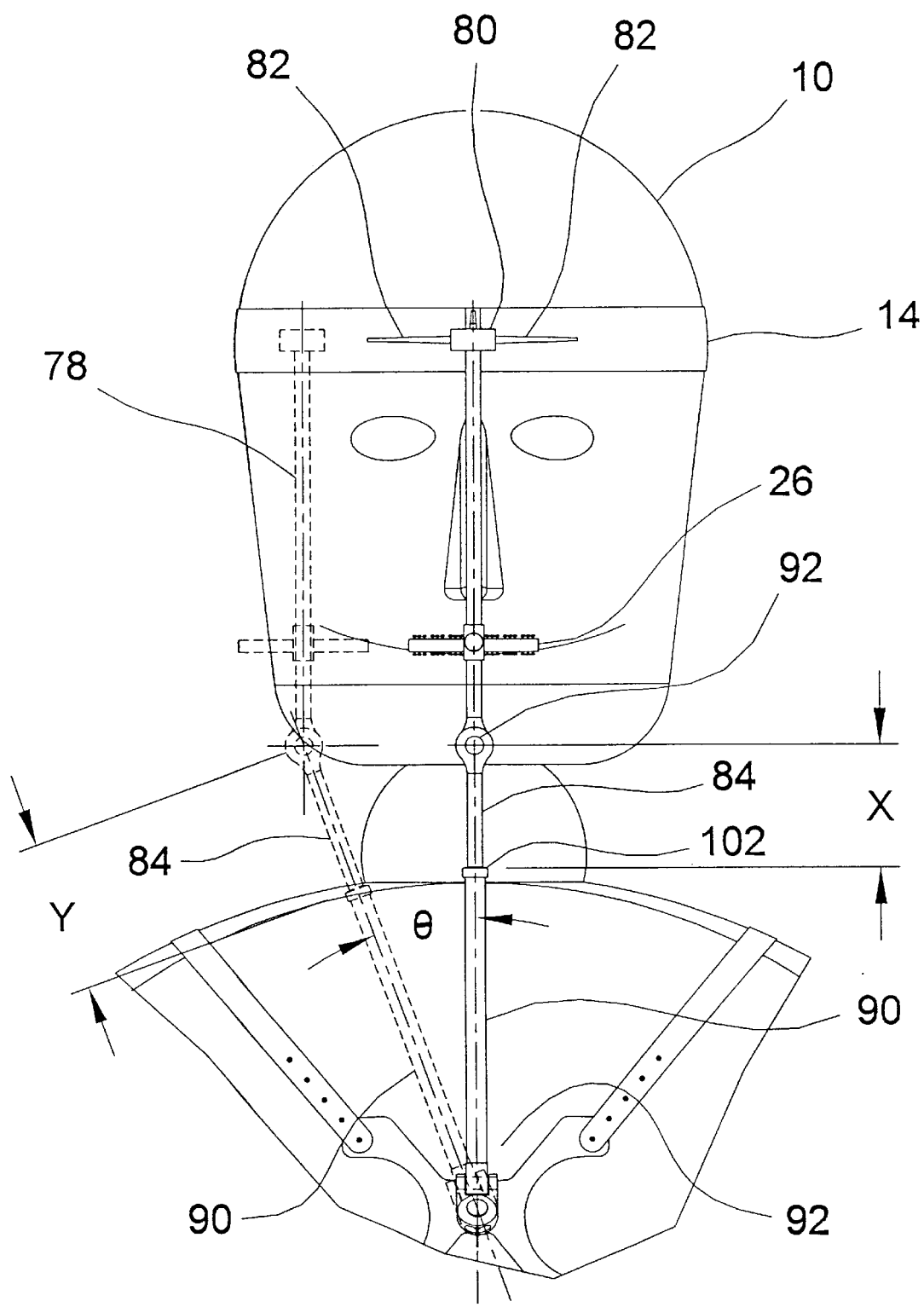
FIG. 25 is a front plan view of the facial and upper chest portions of the patient of FIG. 19, showing how the apparatus accommodates lateral movement of the patient's head.

A circumferential groove 96 extends around the lower end of rod 84. Spring 98 extends within tubular rod 90 between the grooved lower end of rod 84 and the closed lower end of rod 90. A pin 100 is fitted through the lower end of rod 84 to hold the upper end of spring 98 in place. Pin 100 and cap 102 also assist in preventing separation of rods 84, 90 if the patient's head is tilted backwardly, due to contact of pin 100 with cap 102 (FIGS. 18, 25). More particularly, cap 102 is fitted over the upper end of rod 90 and is apertured to permit passage of rod 84 through cap 102 and thus accommodate vertical motion of rods 84, 90 relative to one another.

Spring 98 is biased to impart a small force to the lower end of rod 84 to assist in extending rod 84 from tubular rod 90 during lateral movement of the patient's head, as illustrated in FIG. 25 by the dashed and solid outline positions of rods 78, 84 and 90. Spring 98 also provides a small amount of pre-load to eliminate possible looseness of universal joint 92.

Advantageously, rods 84 and 90 are formed of a flexible material to further assist in accommodating movement of the patient's head. This is because the upper end of rod 78 is fixed and remains generally parallel and vertically oriented with respect to the patient's face. Patient movement which might otherwise cause slight binding of parts incorporated in apparatus 12C is accommodated if rods 84 and 90 are flexible as aforesaid. One way to provide the desired flexibility is to form rod 78 from a relatively thick wall stainless steel tubing and form rods 84, 90 from a relatively thin wall stainless steel tubing. The thinner wall material yields a lower polar moment of inertia about the neutral axis of the tubing which is less resistant to flexing.

The components which make up universal joint 92 are shown in FIG. 24. Tubular member 104 is slidably fitted over the end of strut 94 and fixed thereto by tightening thumb screw 106. Ball 108 on the end of thumb screw 106 is received within concave depression 110 in friction shoe 112 which is in turn clamped against strut 94 by the aforementioned tightening of thumb screw 106. Universal joint body member 114 is slidably fitted over tubular member 104 before thumb screw 106 is tightened as aforesaid. A slot 116 is provided in universal joint body 114 to accommodate insertion and fastening of thumb screw 106 as aforesaid. Universal joint body member 114 can be slidably advanced forwardly or rearwardly along tubular member 104 to locate those two parts in a desired position relative to one another. When thumb screw 106 is tightened as aforesaid, universal joint body member 114 is substantially fixed relative to tubular member 104 except as permitted by relative motion of the thumb screw's shaft within slot 116.

As shown in FIG. 25, universal joint 92 accommodates lateral movement of the patient's head by allowing rods 84, 90 to pivot through angle θ relative to the vertical as depicted in FIG. 25. The displacement "Y" between pin 86 and cap 102 varies as X/cosθ, where "X" is the displacement between pin 86 and cap 102 when apparatus 12C is in the vertical position with the patient facing forward and the head inclined neither forwardly nor backwardly.

Figure 26:
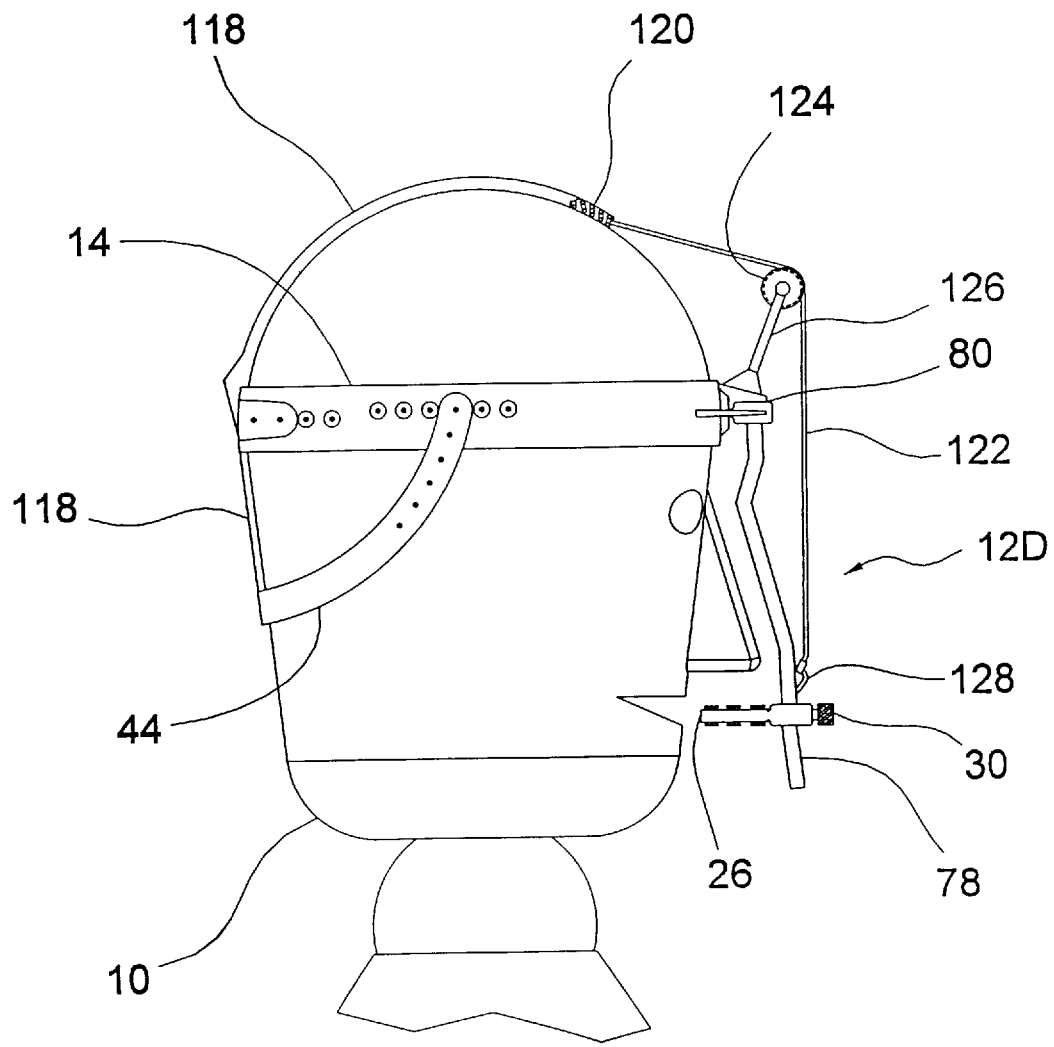
FIG. 26 is a side elevation view which schematically depicts the head of a patient wearing an orthodontic protraction appliance constructed in accordance with a fifth embodiment of the invention.

FIG. 26 depicts a fifth embodiment of the invention, namely orthodontic protraction appliance 12D, which does not require a chest brace. Components of apparatus 12D which are identical to corresponding components of apparatus 12 depicted in FIGS. 1–7E and/or identical to corresponding components of apparatus 12A depicted in FIGS. 8–11 and/or identical to corresponding components of apparatus 12B depicted in FIGS. 12–17 and/or identical to corresponding components of apparatus 12C depicted in FIGS. 18–25 have been given identical reference numerals in FIGS. 18–24 and will not be described further.

A flexible plastic tube 118 is anchored at its rearward end to head band 14 and/or secondary strap 44. A spring 120 is fixed within the opposed forward end of tube 118. The length of tube 118 is selected such that spring 120 will be positioned atop the central forward portion of the patient's head when apparatus 12D is worn as illustrated. Head band 14, secondary strap 44 and tube 118 thus form a simple helmet. One end of flexible cable 122 is fixed to spring 120. Cable 122 is entrained over roller 124 which is supported on strut 126 fixed to socket 80. The opposite end of cable 122 is fixed to hook 128 which is in turn fixed to rod 78 immediately above elastic support plate 26. The length of cable 122 is adjusted to tension cable 122 sufficiently to bias the lower end of rod 78 and support plate 26 forwardly and away from the patient's mouth, thereby counteracting any tendency of elastic bands (not shown) coupled between elastic support plate 26 and braces (not shown) fixed to the patient's teeth to draw elastic support plate 26 toward the patient's mouth, thus maintaining generally consistent tension in the elastic bands.

Figure 27:
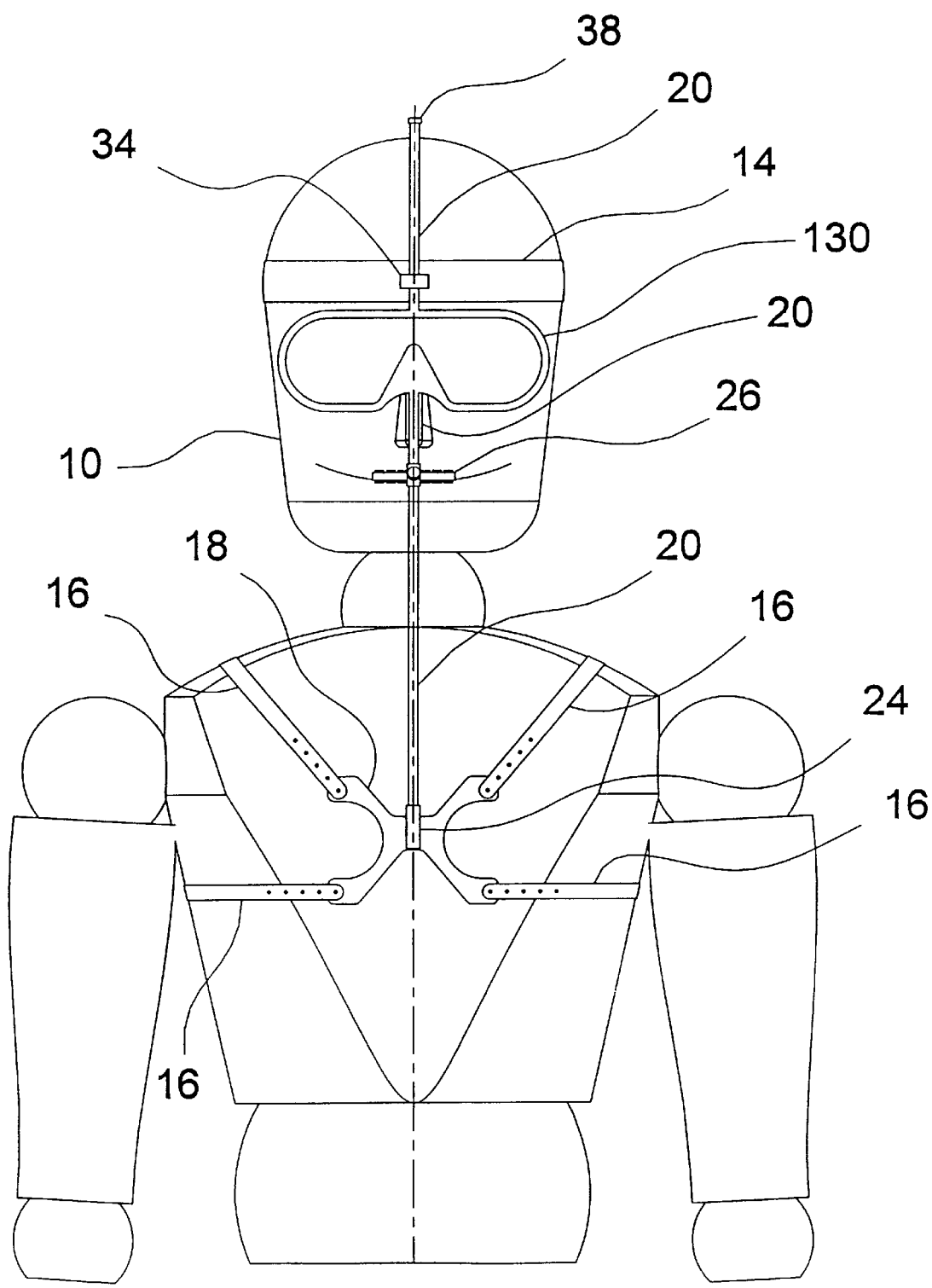
FIG. 27 is a front elevation view of the patient and apparatus of FIG. 2 adapted to include a vision port.

All embodiments of the invention may be adapted to include a vision port 130, as shown in FIG. 27, to reduce obstruction of the patient's vision. Port 130 is formed integrally with rod 20, such that port 130 is positioned around the patient's eyes when the apparatus is worn as illustrated. Rod 20 extends above and below, but not through, port 130 and thus does not obstruct the patient's vision through port 130. The size and shape of port 130 are such that the patient has comfortable, substantially unobstructed vision through port 130 when the apparatus is worn as illustrated.

As will be apparent to those skilled in the art in the light of the foregoing disclosure, many alterations and modifications are possible in the practice of this invention without departing from the spirit or scope thereof. For example, although the foregoing disclosure mentions usage of the invention only with "braces" applied to the patient's teeth, persons skilled in the art will understand that the invention is well suited to usage with other types of dental appliances including removable appliances such as twin block, split plate, bionator and cast chrome cobalt appliances, and fixed appliances such as space maintainer, rapid maxillary expander, two-by-four and two-by-six appliances. Accordingly, the scope of the invention is to be construed in accordance with the substance defined by the following claims.

What is claimed is:

1. An orthodontic protraction appliance, comprising:
   (a) a first rod;
   (b) a first support for supporting an upper portion of said first rod against a patient's forehead, said first support further comprising:
      (i) a head band coupled to said upper portion of said first rod, said head band for encircling the patient's head to support said upper portion of said first rod against said patient's head;
      (ii) a first strut coupled between said upper portion of said first rod and said head band, said first strut further coupled to said upper portion of said first rod to permit unimpeded vertical movement of said first rod with respect to said head band, one end of said first strut fixed to said head band, an opposed end of said first strut fixed to a first ring, said first ring encircling said upper portion of said first rod;
   (c) a second support for supporting a lower portion of said first rod against the patient's chest, said second support further comprising:
      (i) a breast plate coupled to said lower portion of said first rod, said breast plate for supporting said lower portion of said first rod against said patient's chest;
      (ii) a chest strap having opposed ends coupled to said breast plate, said chest strap for encircling said patient's chest to support said breast plate;
      (iii) a second strut coupled between said lower portion of said first rod and said breast plate; and,
   (d) a third support coupled to a central portion of said first rod to support a plurality of elastics between said third support and a dental appliance coupled to the patient's teeth.

2. An orthodontic protraction appliance as defined in claim 1, wherein said second strut is flexible.

3. An orthodontic protraction appliance as defined in claim 2, wherein:
   (a) one end of said second strut is fixed to said breast plate;
   (b) an opposed end of said second strut is fixed to said lower portion of said first rod; and,
   (c) said second strut has a reduced cross-sectional area in a central region of said second strut between said ends of said second strut.

4. An orthodontic protraction appliance as defined in claim 1, further comprising a shoulder harness coupled between said breast plate and said chest strap, said shoulder harness for extending over the patient's shoulders to further support said breast plate.

5. An orthodontic protraction appliance as defined in claim 1, said first rod having a top end diameter exceeding said first ring diameter.

6. An orthodontic protraction appliance as defined in claim 1, further comprising a second rod, said second rod having an upper portion coupled to said first support and a lower portion coupled to said third support.

7. An orthodontic protraction appliance as defined in claim 6, wherein said third support is slidably positionable along and releasably fastenable to said second rod.

8. An orthodontic protraction appliance as defined in claim 7, wherein
   said head band is further for encircling said patient's head to support said upper portion of said second rod against said patient's head.

9. An orthodontic protraction appliance as defined in claim 8, wherein said second strut is flexible.

10. An orthodontic protraction appliance as defined in claim 9, wherein:
    (a) one end of said second strut is fixed to said breast plate;
    (b) an opposed end of said second strut is fixed to said lower portion of said first rod; and,
    (c) said second strut has a reduced cross-sectional area in a central region of said second strut between said ends of said second strut.

11. An orthodontic protraction appliance as defined in claim 8, further comprising a shoulder harness coupled between said breast plate and said chest strap, said shoulder harness for extending over the patient's shoulders to further support said breast plate.

12. An orthodontic protraction appliance as defined in claim 8, said first rod having a top end diameter exceeding said first ring diameter.

13. An orthodontic protraction appliance as defined in claim 6, wherein said third support is coupled to said central portion of said first rod to permit unimpeded vertical movement of said first rod with respect to said third support.

14. An orthodontic protraction appliance as defined in claim 13, said third support further comprising a second ring encircling said central portion of said first rod.

15. An orthodontic protraction appliance as defined in claim 6, wherein said second rod upper portion is pivotally coupled to said first support.

16. An orthodontic protraction appliance as defined in claim 6, further comprising lateral alignment means coupled between said central portion of said first rod and said lower portion of said second rod, said lateral alignment means for maintaining lateral alignment of said third support with respect to said first rod during vertical movement of said first rod with respect to said third support.

17. An orthodontic protraction appliance as defined in claim 16, said lateral alignment means further comprising a sector having a longitudinally extending, concave groove in a rearward, convex arc portion of said sector, said groove positioned against said central portion of said first rod for rotatable movement of said sector along said groove with respect to said central portion of said first rod, said sector having a forward portion pivotally coupled to said lower portion of said second rod.

18. An orthodontic protraction appliance as defined in claim 17, wherein said third support and said sector forward portion are slidably positionable along and releasably fastenable to said second rod.

19. An orthodontic protraction appliance as defined in claim 17, wherein said sector forward portion is eccentrically pivotally coupled to said lower portion of said second rod.

20. An orthodontic protraction appliance as defined in claim 17, said third support further comprising a second ring encircling said central portion of said first rod.

21. An orthodontic protraction appliance as defined in claim 20, said second ring further encircling said convex arc portion of said sector.

22. An orthodontic protraction appliance as defined in claim 6, further comprising a vision port in said first rod and in said second rod, wherein said vision port is positioned around the patient's eyes during wearing of said protraction appliance, and wherein said vision port is sized and shaped for substantially unobstructed viewing by the patient through said vision port during wearing of said appliance.

23. An orthodontic protraction appliance as defined in claim 1, wherein
a ball and socket joint couples an opposed end of said second strut to said lower portion of said first rod.

24. An orthodontic protraction appliance, comprising:
   (a) a first rod;
   (b) a first support for supporting an upper portion of said first rod against a patient's forehead;
   (c) a second support for supporting a lower portion of said first rod against the patient's chest; and,
   (d) a third support coupled to a central portion of said first rod to support a plurality of elastics between said third support and to said a dental appliance coupled to the patient's teeth;
wherein a lower end of said upper portion of said first rod is pivotally connected to an upper end of said lower portion of said first rod to permit lateral movement of said upper and lower portions of said first rod with respect to said patient while substantially preventing forward or rearward movement of said upper or lower portions of said first rod with respect to said patient.

25. An orthodontic protraction appliance as defined in claim 24, wherein said upper portion of said first rod is shaped to conform generally to a central vertical side profile of a human face.

26. An orthodontic protraction appliance as defined in claim 24, wherein said second support further comprises:
   (a) a breast plate for supporting said lower portion of said first rod against said patient's chest; and,
   (b) pivotal coupling means for pivotally coupling a lower end of said lower portion of said first rod to said breast plate.

27. An orthodontic protraction appliance as defined in claim 26, wherein said pivotal coupling means further comprises a universal joint for permitting lateral movement of said lower portion of said first rod with respect to said patient while substantially preventing forward or rearward movement of said lower portion of said first rod with respect to said patient.

28. An orthodontic protraction appliance as defined in claim 27, further comprising spring biasing means coupled between said universal joint and said lower end of said lower portion of said first rod, said spring biasing means for extending said lower portion of said first rod away from said universal joint as said lateral movement increases and for retracting said lower portion of said first rod toward said universal joint as said lateral movement decreases.

29. An orthodontic protraction appliance as defined in claim 28, wherein:
   (a) said first support further comprises a head band for encircling said patient's head to support said upper portion of said first rod against said patient's head; and,
   (b) an upper end of said upper portion of said first rod is fixed to said head band.

30. An orthodontic protraction appliance, comprising:
   (a) a rod;
   (b) a first support for supporting an upper portion of said rod against a patient's forehead;
   (c) a second support for biasing a lower portion of said rod forwardly and away from the patient's mouth; and,
   (d) a third support coupled to a lower portion of said rod to support a plurality of elastics between said third support and a dental appliance coupled to the patient's teeth.

31. An orthodontic protraction appliance as defined in claim 30, wherein:
   (a) said first support further comprises a head band fixed to said upper portion of said rod, said head band for encircling the patient's head to support said upper portion of said rod against said patient's head; and,
   (b) said second support further comprising a cable coupled between said head band and said lower portion of said rod.

32. An orthodontic protraction appliance as defined in claim 31, further comprising a spring coupled to said cable, said spring for applying a tension force to said cable.

33. An orthodontic protraction appliance as defined in claim 32, wherein said spring is further coupled between said head band and an upper end of said cable.

34. An orthodontic protraction appliance as defined in claim 33, said first support further comprising a strut for supporting said cable away from said upper end of said rod.

35. An orthodontic protraction appliance as defined in claim 34, further comprising a roller on said strut for rotatably supporting said cable between said head band and said lower end of said rod.

36. An orthodontic protraction appliance as defined in claim 35, wherein said third support is slidably positionable along and releasably fastenable to said rod.

37. An orthodontic protraction appliance as defined in claim 30, further comprising a vision port in said rod, wherein said vision port is positioned around the patient's eyes during wearing of said appliance, and wherein said vision port is sized and shaped for substantially unobstructed viewing by the patient through said vision port during wearing of said protraction appliance.

38. An orthodontic protraction appliance comprising:
   (a) a first rod;
   (b) a first support for supporting an upper portion of said first rod against a patient's forehead;
   (c) a second support for supporting a lower portion of said first rod against the patient's chest;
   (d) a third support coupled to a central portion of said first rod to support a plurality of elastics between said third support and a dental appliance coupled to the patient's teeth; and, (e) a vision port in said first rod, wherein said vision port is positioned around the patient's eyes during wearing of said protraction appliance, and wherein said vision port is sized and shaped for substantially unobstructed viewing by the patient through said vision port during wearing of said appliance.

* * * * *